United States Patent
Meyer et al.

(10) Patent No.: US 6,187,285 B1
(45) Date of Patent: Feb. 13, 2001

(54) METAL CHELATES OF SUBSTITUTED POLYAMINOCARBOXYLIC MACROCYCLES AND THEIR USE IN DIAGNOSTIC IMAGING

(75) Inventors: Dominique Meyer, Saint-Maur; Marc Port, Deuil la Barre; Olivier Rousseaux, Senlis; Christian Simonot, Paris, all of (FR)

(73) Assignee: Guerbet, Villepinte (FR)

( * ) Notice: Under 35 U.S.C. 154(b), the term of this patent shall be extended for 0 days.

(21) Appl. No.: 09/207,513

(22) Filed: Dec. 9, 1998

(30) Foreign Application Priority Data

Dec. 10, 1997 (FR) .................................................. 97 15642

(51) Int. Cl.$^7$ .......................... A61B 5/055; A61K 51/00; A61K 49/04
(52) U.S. Cl. .................... 424/1.65; 424/9.363; 424/9.42; 540/465; 540/474; 514/184; 514/836
(58) Field of Search ..................... 540/465, 474; 424/9.363, 1.65, 9.42; 514/836, 184; 436/173; 600/420

(56) References Cited

U.S. PATENT DOCUMENTS

| | | | |
|---|---|---|---|
| 5,474,756 | * 12/1995 | Tweedle et al. .................. | 424/9.363 |
| 5,628,982 | * 5/1997 | Lauffer et al. ................... | 424/9.363 |
| 5,648,063 | * 7/1997 | Gries et al. ...................... | 424/9.363 |
| 5,708,166 | * 1/1998 | Uggeri et al. .................... | 540/474 |
| 5,798,089 | * 8/1998 | Varadarajan et al. ............. | 424/1.65 |
| 5,871,699 | * 12/1998 | Maier et al. ..................... | 424/9.363 |
| 5,871,709 | * 2/1999 | Gries et al. ...................... | 424/1.65 |
| 5,876,698 | * 3/1999 | Schmitt-Willich et al. ....... | 424/9.363 |
| 5,900,228 | * 5/1999 | Meade et al. .................... | 424/9.363 |

FOREIGN PATENT DOCUMENTS 0 661 279  6/1995  (EP) .
2 736 051  1/1997  (FR) .

* cited by examiner

Primary Examiner—Gary E. Hollinden
(74) Attorney, Agent, or Firm—Jacobson, Price, Holman & Stern, PLLC

(57) ABSTRACT

Chelates of the compounds of formula I

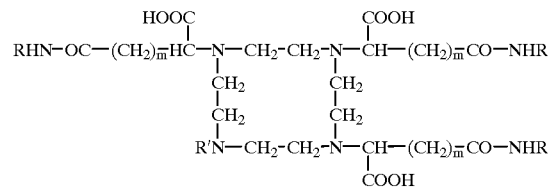

in which R is a hydrophilic group containing 3 or 4 successive phenyl rings and m is 1 or 2, with metal ions, for use in diagnostic imaging.

12 Claims, No Drawings

METAL CHELATES OF SUBSTITUTED POLYAMINOCARBOXYLIC MACROCYCLES AND THEIR USE IN DIAGNOSTIC IMAGING

The present invention relates to chelates formed from macrocyclic polyaminocarboxylic acids with metal cations and to their use in diagnostic imaging, in particular magnetic resonance imaging (MRI) for magnetic cations.

The relaxivities $r_1$ and $r_2$ and particularly the first give a measure of the magnetic efficacy of such a chelate and make it possible to assess its use as a contrast agent. For the products currently marketed, $r_1$ does not exceed 6 mM$^{-1}$s$^{-1}$ (at 20 MHz and 37° C.), whether the chelates are linear (gadopentetate or DTPA and gadoversetamide) or macrocyclic (gadoterate or DOTA and gadoteridol). In addition, when these compounds are administered intravenously, they diffuse rapidly from the vascular domain into the extracellular interstitial compartment and there is not yet a product on the market which remains sufficiently localized in blood vessels to allow an accurate evaluation of tissue perfusion, of capillary permeability or of the blood volume.

Substituted macromolecules resulting from the grafting of a standard chelate onto a biocompatible polymer, such as that obtained by attaching gadopentetate to polyethylene glycol or polylysine, or of gadopentetate and gadoterate onto a polysaccharide, which have been described for more than 10 years and which have been tested on animals, have still not been developed in man.

It has since been proposed to graft these standard chelates (DTPA or DOTA) onto branched polymers of unique molecular mass, known as cascade polymers or dendrimers, consisting of varied repeating units, such as, for example, in EP-A-430,863 or EP-A-607222. It is mentioned that the relaxivities of these products are high and that they have a certain level of vascular retention, but these results remain limited since, for example, the polyamines bearing 24 or 48 gadopentetate molecules described in EP-A-430,863 have, despite their size, only a relaxivity $r_1$ of about 13 mM$^{-1}$s$^{-1}$ for 4.8 mM$^{-1}$s$^{-1}$ for gadopentetate alone; in addition, it appears to be difficult to isolate a single compound during the synthesis, i.e. to obtain the substitution of all of the end groups of such a polyamine, assuming that it was possible to obtain it in uniform molecular weight, which would avoid the dispersity of the physicochemical and pharmacokinetic properties of the components of the dose administered, which is a known drawback of the standard substituted polymers, which has limited their development.

In the most recent studies aimed at obtaining molecules with high relaxivity, of unique molecular weight and containing only one chelating group, mention may be made of EP-A-661,279 and WO 97/01359, which underline the advantage of introducing, into the known molecular structures, at least 3 hydrophilic side arms with a weight of greater than 200 onto the side groups of the donor nitrogen atoms which bear the other coordinating groups, whether they are acidic groups or substituted groups; in particular, it is mentioned that the gadolinium complexes of the substituted compounds of the gadoterate of formula

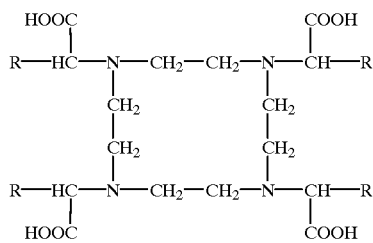

in which

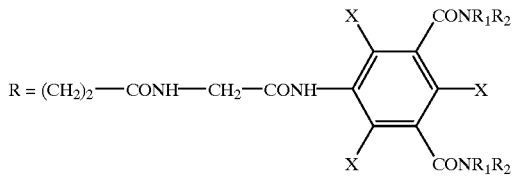

have a relaxivity $r_1 > 20$ mM$^{-1}$s$^{-1}$ at 20 MHz and 37° C.

As compounds with high relaxivity and having a certain level of vascular retention, mention should also be made of those described in WO 96/23526, which are substantially different in structure from the above compounds, one of the representatives of which, MS325, a gadolinium complex of the compound of formula

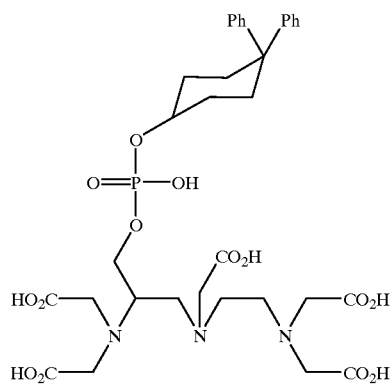

binds reversibly to albumin in plasma such that its relaxivity $r_1$ in this medium is virtually 10 times that of the gadopentetate from which it is derived, for a half-life multiplied by 4 and a distribution volume divided by 2.5 in rabbits, according to Acad. Radiol. S356–S358 (1996).

In contrast with MS325 and its homologues, the paramagnetic metal complexes of the present invention have high relaxivities, even in water, since $r_1$ therein is greater than 30 mM$^{-1}$s$^{-1}$ (20 MHz, 37° C.); in addition, although they hardly bind to plasmatic albumin at all, they show marked vascular localization and are mainly eliminated via the kidneys, such that they can advantageously be used in MRI as contrast agents, for revealing the circulatory system.

According to a first aspect, the invention relates to the paramagnetic, or radioactive, metal ion chelates of the polyaminocarboxylic macrocycles of formula

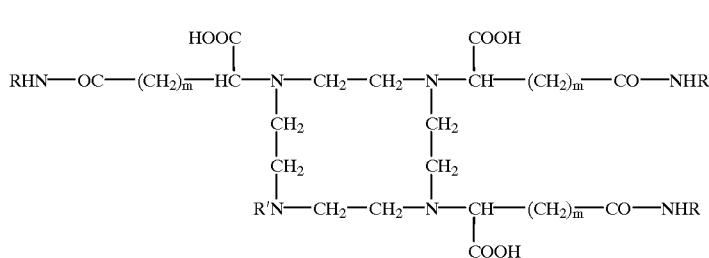

(I)

in which
m is 1 or 2,
R' is H, an optionally hydroxylated $C_1$–$C_4$ alkyl group, a $CH_2$—COOH group, a group $CH_2$—$CONZ_1Z_2$, $Z_1$ and $Z_2$ being, independently of each other, H or an optionally hydroxylated $C_1$–$C_4$ alkyl group,
or R' is a group HOOC—CH—$(CH_2)_m$—CONHR, R is a group

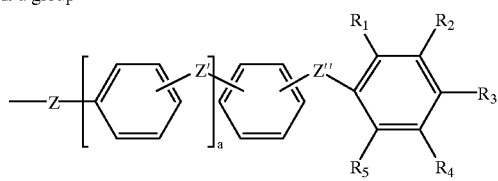

in which a is 1 or 2
Z is a bond, $CH_2$, $CH_2$—CO—NH or $(CH_2)_2$—NHCO
Z' is a bond, O, S, NQ, $CH_2$, CO, CO—NQ, NQ—CO, NQ—CO—NQ, CO—NQ—$CH_2$—CONQ
Z" is CO—NQ, NQ—CO, CO—NQ—$CH_2$—CO—NQ or NQ—CO—$CH_2$—NQ—CO
where Q is H or an optionally hydroxylated $C_1$–$C_4$ alkyl group
$R_1$, $R_2$, $R_3$, $R_4$ and $R_5$, independently of each other, are selected from the group consisting of H, Br, Cl, I, CO—$NQ_1Q_2$ or $N(Q_1)$—CO—$Q_2$ and $Q_1$ and $Q_2$, which may be identical or different, are selected from $C_2$–$C_6$ alkyl groups which are optionally hydroxylated and optionally interrupted by an oxygen atom, such that $Q_1$ and $Q_2$ together contain from 4 to 10 OH groups, with the proviso that at least 1, and not more than 2, groups $R_1$, $R_2$, $R_3$, $R_4$ and $R_5$ are amido groups.

The metal cations complexed in the chelates of the invention are selected from the paramagnetic cations generally used in MRI, especially trivalent cations including $Fe^{3+}$, $Cr^{3+}$, $Eu^{3+}$, $Gd^{3+}$, $Tb^{3+}$, and particularly $Gd^{3+}$, or, for use in scintigraphy, from the cations of radio isotopes such as $^{99m}Tc$ or $^{111}In$.

Inorganic bases which may give a pharmacologically acceptable salt with the optional free acid group of a metal complex of the compound of formula I are preferably selected from alkali metal ($K^+$, $Na^+$) or alkaline-earth metal ($Ca^{++}$, $Mg^{++}$) hydroxides and carbonates, while the organic bases are chosen from amines such as aminoethanol, thromethamine or N-methylglucamine, of from amino acids such as lysine, glycine or arginine.

The preferred compounds are those in which m is 2 and a is 1, R' is not H or alkyl, Z is a bond, $CH_2$ or $CH_2CONH$, Z' is CONH, NHCO, $CONHCH_2CONH$ or $NHCONH$, Z" is CONH or $CONHCH_2CONH$ with $R_3$=$CONQ_1Q_2$ and $R_1$, $R_2$, $R_4$ and $R_5$ are, independently, H, Br, Cl or I, or $R_2$=$R_4$=$CONQ_1Q_2$ in which case $R_1$, $R_3$ and $R_5$ are, independently, H, Br, Cl or I,
or Z" is NHCO with $R_3$=$N(Q_1)COQ_2$ and $R_1$, $R_2$, $R_4$ and $R_5$ are, independently, H, Br, Cl or I, or $R_2$=$R_4$=$N(Q_1)COQ_2$, in which case $R_1$, $R_3$ and $R_5$ are, independently, H, Br, Cl or I.

Among these, the preferred compounds are those in which Z' is CONH, $CONHCH_2CONH$ or NHCONH, and, better still, those in which Z' is CONH, shorter bond, $R_1$, $R_3$ and $R_5$ are all Br or I and $R_2$=$R_4$=$CONQ_1Q_2$ where $Q_1$ and $Q_2$ are $C_2$–$C_6$ hydroxyalkyl groups together containing 6 to 10 OH groups or, if $Q_1$ and/or $Q_2$ is interrupted by an oxygen atom, they contain from 4 to 8 OH groups.

According to a second aspect, the invention relates to a process for preparing metal chelates of the compounds of formula I, which consists in reacting a chelate II of the metal cation $M^{3+}$ and of the compound of formula

II'

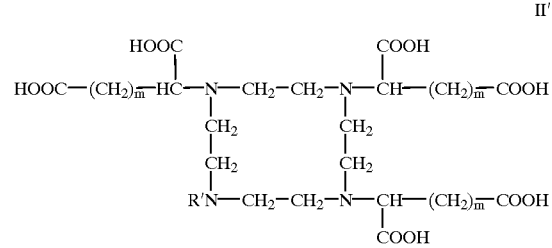

with an amine of formula

III

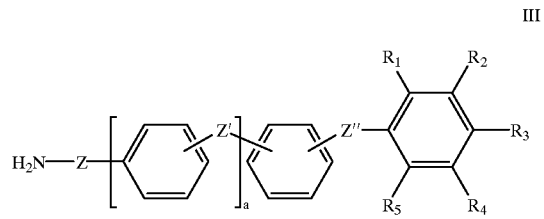

in which the letters have the same meanings as in formula I, in the presence of a coupling agent, in particular those used in peptide synthesis, which is suited to the aqueous or organic reaction medium in which the compounds of formulae II and III are, at least partially, in solution. Under these conditions, the protected carboxylic acid groups located on the carbon atoms alpha to the nitrogen atoms in compound II do not react.

According to another aspect, the invention relates to the contrast agents for imaging in man or animals by scintigraphy when the chelate is radiolabelled, or by magnetic resonance when the chelate contains a paramagnetic ion, optionally in the form of a salt of an inorganic or organic cation, in a pharmaceutically acceptable vehicle, combined with compatible excipients.

According to a final aspect, the invention relates to imaging methods for the human or animal body, which consist in administering an effective unit dose of a composition of the invention to an individual and in subjecting the tissue or the area to be studied to a suitable magnetic field in order to observe the proton magnetic resonance, or to scintigraphy when the chelate contains a radionuclide.

The chelates of the compounds of formula I which contain 4 identical substituents on the nitrogen atoms of the central macrocycle, 1,4,7,10-tetraazacyclododecane, or cyclen, are prepared in fewer steps than in the cases in which R' represents H, $CH_2COOH$, $CH_2CONZ_1Z_2$ or a $C_1$–$C_4$ alkyl or hydroxyalkyl group, such as $CH_3$, $CH_2CH_2OH$ or $CH_2$—CHOH—$CH_2OH$, since one of the 4 nitrogen atoms of cyclen has to be temporarily selectively protected with a leaving group or a monosubstitution of the macrocycle with the group R' has to be carried out beforehand.

The groups R in the compounds of the invention contain 3 or 4 phenyl rings, of which the one most remote from the macrocycle is substituted with one or more hydrophilic groups, which have an influence on the water solubility and the biocompatibility of the chelate. Among these hydrophilic groups, the preferred ones are tertiary amide groups, in which the substituents are $C_2$–$C_6$ hydroxyalkyl groups optionally interrupted by an oxygen atom, and more particularly those derived from linear amino alcohols $HNQ_1Q_2$ in which $Q_1$ and $Q_2$, independently of each other, are $CH_2(CHOH)_n(CH_2OCH_2)_r(CHOH)_pCH_2OH$, and, if, in $Q_1$ and $Q_2$, r=0, then p=0 and n can be 0 to 4 and $Q_1$ and $Q_2$ together contain from 5 to 10 OH groups, which corresponds, in particular for $HNQ_1Q_2$, to H—N[$CH_2$(CHOH)$_4$CH$_2$OH]$_2$ and

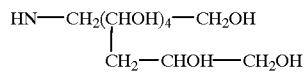

if, in $Q_1$ and/or $Q_2$, r=1, then n and p are, independently of each other, 0 or 1 and $Q_1$ and $Q_2$ together contain from 4 to 8 OH groups,
which corresponds, in particular for $HNQ_1Q_2$, to

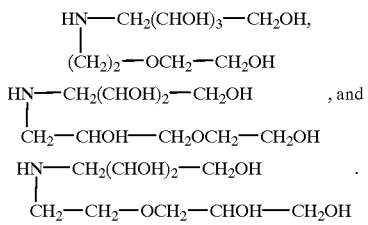

These amino alcohol precursors are commercially available or can be prepared
either from the appropriate primary amino alcohol, for example by the reaction of a sugar and reduction as described in EP-A-675,105 when n=4 and p=r=0, or for those in which n=3 and p=r=0, as described in EP-A-558,395,
or by the reaction of a sugar on benzylamine, followed by introduction of the second hydroxylated substituent by the reaction of a suitable halide or sulphonate, followed by removal of the benzyl by catalytic hydrogenation.

When $Q_1$ and/or $Q_2$ contain an oxygen atom in the chain, the amino alcohols are, when n=p=0, prepared from 2-aminoethoxyethanol which can be reacted with a suitable hydroxylated alkyl halide or epoxide or alternatively a hydroxylated aliphatic aldehyde such as a monosaccharide, in order to form an imine, which is then reduced catalytically or chemically.

When n=1, the amino alcohols can be prepared by the reaction of the epoxide

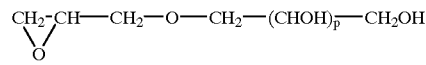

on the appropriate primary amino alcohol, the said epoxides being obtained by oxidation of the corresponding substituted ethylenes with a peracid or a peroxyimidic acid, as described in J. Org. Chem. 26 659–663 (1961) and 48 888–890 (1983).

The presence of halogen atoms next to amide groups on the phenyl ring is advantageous and the preferred groups R are those in which $R_1$=$R_3$=$R_5$=Br or I and $R_2$=$R_4$=CO—$NQ_1Q_2$, in particular for their stability.

The bridge Z" can be formed between the two phenyl rings before or after the bridges Z'.

For example, the compound

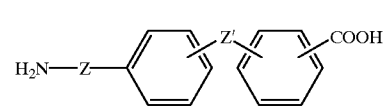

can be prepared, when Z is a bond, from diphenyl derivatives V or esters thereof

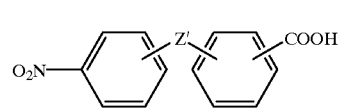

in which Z' has the same meaning as in formula I.

The compound V in which Z' is 0 is described in Makromoleculare Chemie 130 103–144 (1969); the compound in which Z' is HN is described in Indian J. Chem. 13 35–37 (1975), the compound in which Z' is $CH_2$ or CO is described in J. Pharm. Sci. 55(3) 295–302 (1966), the compound in which Z' is a bond is described in Synth. Comm. 24(22) 3307–3313 (1994), and the compound in which Z' is S is described in Il Farmaco, 44(7–8) 683–684 (1989).

Other compounds V can be prepared by similar processes: for example, when Z' is HNCONH, by the reaction of $O_2NC_6H_4NCO$ with $H_2NC_6H_4COOH$ in anhydrous medium, or when Z' is NHCO or CONH, by reaction of the aromatic acid chloride with the appropriate aniline dissolved in an aprotic solvent such as $CH_2Cl_2$, $C_6C_5CH_3$, $CH_3CON(CH_3)_2$, or reaction of the aromatic acid with the aniline in the presence of a sulphonic acid chloride, triethylamine and dimethylaminopyridine, as described in Synth. Communications 25(18) 2877–2881 (1995).

Reduction of the $NO_2$ group into $NH_2$ can be carried out, in a known manner, with hydrogen in the presence of a catalyst, or chemically.

When Z in formula IV is $CH_2$—CONH, activated glycine, in which the $NH_2$ group is protected, is reacted with compound IV in which Z is a bond or with an aniline bearing a precursor group of Z', which is optionally protected. The glycine is protected, for example, in the form of carbamate, in particular t-butylcarbamate (Synthesis, 48, 1986) and benzylcarbamate (Chem., Ber., 65, 1192 (1932)), in the form of phthalimide (Tetrahedron Letters 25, 20, 2093–2096

(1984)), with a benzyl (Bull. Soc. Chim. Fr., 1012–1015, (1954)), an N-allyl (Tetrahedron Letters 22, 16, 1483–1486 (1981)). (See also Protective groups in organic synthesis 315–349, T. W. Greene (John Wiley & Sons Inc.).)

Removal of the protecting group from the $NH_2$ attached to Z is generally carried out only at the stage of compound III. Conventionally, a phthalimido group is removed by the action of hydrazine, whereas a benzyloxycarbonyl or benzyl group is removed by catalytic hydrogenation.

When $Z=CH_2$ in the compound IV and $Z'=CONH$ or $CONHCH_2CONH$, 4-aminomethylbenzoic acid, in which the $NH_2$ group is protected in the form of carbamate or imide, can be reacted, as described in J. Org. Chem. 43, 2320–2325 (1978) or in Rec. Trav. Chim. Pays-Bas, 79, 688 (1960) on the suitably substituted protected benzoic acid.

When Z is $(CH_2)_2NHCO$, the compound III can be prepared by the action of an excess of ethylene diamine on a suitable benzoic ester, either bearing the substituted (Z'-phenyl)$_a$—Z"-phenyl chain or bearing only one optionally protected precursor group of Z'.

Moreover, when a is equal to 2, compound IV in which the amino group is optionally protected can be reacted with an aminobenzoic acid whose acid function is optionally protected, to give the compounds IV' in which the second Z' is CONH of formula

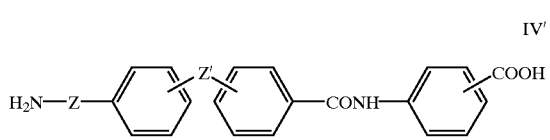

IV'

The compounds IV or IV' are then reacted with the suitably substituted terminal phenyl ring of formula

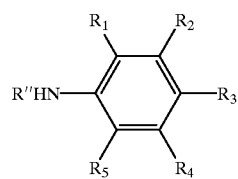

VI in which $R_1$, $R_2$, $R_3$, $R_4$ and $R_5$ are H, halogen, $CO—NQ_1Q_2$ as in formula I or are optionally protected and R" represents $CO—CH_2—NH_2$ or H, in organic or aqueous solution, the compounds IV or IV' being either in the form of acid chloride or in the presence of a coupling agent, such as those used in peptide synthesis, and, for example, an aliphatic carbodiimide, a sulphochloride or a chloroformate, optionally bearing a solubilizing quaternary ammonium or amino group.

The amide of formula VI in which R"=H is prepared by methods known to those skilled in the art starting with a suitable, optionally halogenated aromatic amino acid, in which each carboxylic group present-is activated in the form of acid chloride or of mixed anhydride, or starting with the nitro aromatic acid which is amidated, after which the $NO_2$ group is reduced.

The compounds VI in which $R_1=R_3=R_5=Br$ or I, and $R_2$ and $R_4=CO—NQ_1Q_2$ where $Q_1=CH_2(CHOH)_4CH_2OH$ and $Q_2=CH_2CH_2OH$ or $CH_2(CHOH)_{1-3}—CH_2OH$ and $R"=CO—CH_2—NH_2$ are described in WO 97/01359. The other halogenated or non-halogenated derivatives, and in particular those in which the chains $Q_1$ and $Q_2$ are interrupted by an oxygen atom, can be prepared in a similar manner starting with suitable amino alcohols.

When Z is a bond, it is preferred to react the nitro compound such as V with the aniline VI before carrying out the reduction.

It is also optionally possible to react the compounds IV or IV' with a compound which is a precursor of VI, containing the COOH group, optionally protected in ester form, in place of the group $CO—NQ_1Q_2$, in order to only subsequently prepare the mono- or diamide, or alternatively to react a compound

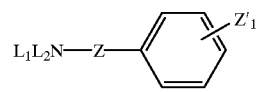

in which $NL_1L_2$ is a protected amino group, with

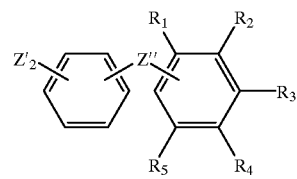

such that $Z'_1$ and $Z'_2$ react to give Z'.

In order to prepare a compound III in which $R_3$ or $R_2$ and $R_4$ represent $N(Q_1)CO—Q_2$ and $Z"=NH—CO$ or $NH—CO—CH_2—NH—CO$, the benzoic acid of formula

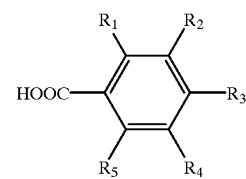

V in which the hydroxyls in the group $N(Q_1)COQ_2$ are optionally protected, can be reacted with an amine

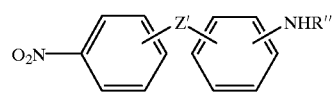

VII in which R" is H or $COCH_2—NH_2$, followed by reduction of the nitro group to give a compound III in which Z is a bond.

Among the compounds of formula V, mention may be made of those prepared from $CH_2(OCOCH_3)CH(OCOCH_3)_4COCl$, described in Org. Synth. 41, 79–82 (1961), and from suitable aminobenzoic acids, or the one in which $R_1=R_3=R_5=I$ and

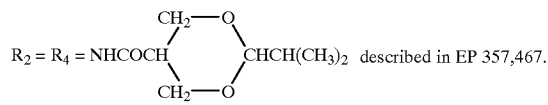

In the amido groups Z' and Z", Q can be introduced in a conventional manner by the reaction of the corresponding halide in the presence of a base with the compound in which Q=H, preferably at the intermediate stages.

Reaction of the compounds of formula III with the salts of the chelates of formula II takes place, preferably in aqueous medium, optionally in the presence of a polar aprotic solvent such as dioxane or tetrahydrofuran, in the presence of a soluble carbodiimide, such as those bearing the amino group, described in J. Org. Chem. 21, 439–441 (1956) and 26, 2525–2528, (1961) or U.S. Pat. No. 3,135,748, or a quaternary ammonium group, in Org. Synth. V, 555–558, which relates to a substituted 1-ethyl-3(3-dimethylamino) propylcarbodiimide (EDCI) or its analogue, 1-cyclohexyl-3-(2-morpholinoethyl)carbodiimide metho-p-tolyl sulphonate. It can also be carried out in the presence of N-hydroxysulphosuccinimide as described in Bioconjugate Chem. 5, 565–576 (1994) or of 2-succinimido-1,1,3,3-tetramethyluronium tetrafluoroborate and analogues described in Tetrahedron Letters 30, 1927–1930 (1989).

Another process consists in forming an intermediate activated ester by reacting, for example, N-hydroxysulphosuccinimide (NHS) or hydroxybenzotriazole (HOBT) in the presence of carbodiimide such as EDCI, with the chelate II which can be dissolved as a salt with an inorganic cation, for example an ammonium or sodium cation.

In the presence of 2-ethoxy-1-ethoxycarbonyl-1,2-dihydroquinoline (EEDQ), the reaction can be carried out in aqueous-alcoholic medium.

The compound of formula II' in which m is 1 can be prepared from cyclen, which is reacted with an acetylene-dicarboxylic acid diester to give an enamine which is reduced by a conventional catalytic or chemical method, followed by hydrolysis of the ester groups. In the case of a benzyl ester, it is preferred, in a first step, to carry out chemical reduction of the enamines, for example by the reaction with a cyanoborohydride, followed by debenzylation with hydrogen in the presence of a catalyst.

The chelate II in which m=2 and the 4 substituents on the nitrogen atoms are identical and $M^{3+}$ is $Gd^{3+}$ is a known compound, described in particular in EP-A-661,279.

The chelate II in which m=1 is prepared by the same processes.

The compounds II in which $M^{3+}$ represents another metal cation will be prepared analogously by the reaction of the metal salt, particularly the chloride, or of the metal oxide, on an aqueous solution of a salt of the ligand, as described in U.S. Pat. No. 5,554,748 and the references cited therein, or in Helv. Chim. Acta 69, 2067–2074 (1986), or by cation exchange when the relative stabilities of the chelates allows this, in particular with an ion-exchange resin.

For the chelates with a radionuclide, a radio isotopic exchange can be carried out by heating a chelate with an inorganic salt of the radioactive metal in ultrapure water and removal of the non-complex cations by passage through a complexing resin. The metal cation of the chelate can also be released by another complexing agent in excess, preferably one giving an insoluble Gd chelate, such as oxalic acid, in order to obtain the pure compound of formula II before complexing another metal cation.

The compounds II' in which m=2 and R' is H, optionally hydroxylated akyl, $CH_2COOH$ and $CH_2CONZ_1Z_2$ can be prepared from cyclen monosubstituted with R' or with a removable protecting group, in which case the introduction of R' takes place after trialkylation with

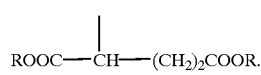

Among the monosubstitution processes, mention may be made of the monoalkylation reaction promoted by the choice of solvent, described in J. Org. Chem. 58, 3869–3876 (1993), the reaction with complexation of 3 nitrogen atoms by boron or phosphorus derivatives, described in Tetrahedron Letters 32(5) 639–641 (1991) and Angew Chem. Int. Ed. 30(5) 560–561 (1991), respectively, or the reaction with formation of an orthoamide intermediate, described in U.S. Pat. No. 5,410,043. When R' is other than H, it is preferable first to introduce R' rather than to carry out the trialkylation of cyclen directly with a reactive derivative of

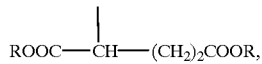

since the dialkyl and tetraalkyl derivatives simultaneously formed cannot be removed by simple operations.

The methods for purifying the various synthetic intermediates and the final product are standard but must, needless to say, be adapted to the chemical nature of the product, to its molecular weight, to its solubilities and to the viscosity of its solutions. Chemical separation methods (selective dissolution, crystallization) or physical methods by filtration on a membrane or by treatment with an adsorbing agent, in suspension or in a column, can be used.

In particular, for the compounds III which are soluble in aqueous medium, they may be purified by passing them through anionic and cationic ion-exchange resins or by ultrafiltration, by diafiltration or by reverse osmosis on a suitably selected membrane in order to remove into the eluate the molecules of low weight, the solvents and the salts.

For the compounds II', it is preferable not to carry out a treatment which can modify the relative proportions of the isomers, and the intermediate esters dissolved in an immiscible organic solvent can be purified by stirring with an aqueous acidic phase and then, after decantation and separation, by placing them in contact with an adsorbent agent, such as silica gel, after which they can be hydrolysed in basic or acidic medium to give the acids II' to be complexed.

The chelates of formula I are generally purified in the form of an alkaline salt which is soluble in aqueous medium, by one of the methods mentioned above, in particular by treating their aqueous solution with carbon black or with silanized silica.

These chelates of the invention are characterized by the presence on the central chelating ring of side arms containing 3 or 4 successive phenyl rings, connected together by short bridges, the final phenyl ring bearing at least one hydrophilic group; despite their high molecular weight and the presence of several hydrophobic phenyl rings, these compounds are water-soluble and biocompatible and can be administered intravenously to man.

In addition, and this is a very important property, they cross the vascular walls to only a small extent, unlike the compounds commmercially available, which makes it possible, during magnetic resonance imaging, to obtain a strong contrast between the vessels and the surrounding tissues; this property, combined with their high relaxivity, makes it possible either to inject lower doses of complexed gadolinium into the patient or to detect pathological states which hitherto could not be clearly demonstrated.

The paramagnetic chelates of the invention can be formulated for a parenteral or enteral administration, combined with pharmaceutical vehicles and excipients that are standard in this field.

For an intravenous or intraarterial administration, the compounds of the invention are in sterile aqueous solution at a concentration of from 0.001 to 0.5 mol/liter, optionally combined with an agent for stabilizing the pH at about 7, such as Tris buffer or $CO_2$, with a tonicity agent such as mannitol, glycerol or glucose, preferably from NaCl which can modify the solubility and dispersion of the chelate, or with another complexing agent such as EDTA.

In order to eliminate the endotoxins which may contaminate the final product, after purification by liquid chromatography in particular, an ultrafiltration is preferably carried out, optionally tangential ultrafiltration at a substantially constant volume, on membranes whose nature and cutoff threshold depends on the molecular weight of the product and on the viscosity pressure of the solution. This purification can also be carried out at certain intermediate steps on compounds of smaller size, by microfiltration, in particular on a ionic membrane, or by ultrafiltration. Treatments with an absorbing agent which may or may not be specific for the endotoxins, such as carbon black, can also be envisaged.

For an intravaginal administration, the aqueous solutions preferably contain a viscosity modifier, such as a natural gum, a polysaccharide or a cellulose derivative. For a rectal administration, the chelate will be formulated as a suppository or a viscous solution. Finally, for an oral administration, it may be formulated as gelatin capsules, tablets or syrup, prepared with the usual excipients. Examples of formulations can be found in Remington's for Pharmaceutical Science, 18th Edition (1990), Mack. Pub. Cy.

The unit dose and its concentration depend on the size of the patient and on the type of imaging carried out, as well as on the solubility, the viscosity in solution, the magnetic efficacy, the capillary wall permeability and the pharmacokinetics of the compound. They will be used in magnetic resonance imaging by applying fast or slow techniques in order to study the perfusion, in particular myocardial, cerebral, renal or hepatic perfusion, for angiograms or in order to visualize or characterize permeability anomalies, in particular tumoral, inflammatory and ischaemic or cartilage anomalies.

These products may also be used in nuclear medicine after introducing a radioactive atom, for example by isotopic exchange of the halogens or of the complexed cation; scintigraphy of the areas to be imaged will be carried after administering the chelates of the invention.

In the text hereinbelow, examples of compounds of the invention are described, as well as a process for preparing the gadolinium chelates of the compounds of formula II in which

R'=H and R'=$CH_2COOH$ and of the phenyl-precursor compounds VI.

Depending on the cases, the recovered products are characterized by their retention distances in thin layer chromatography or their retention times ($t_r$) in high performance liquid chromatography (HPLC) or in steric exclusion chromatography (SEC). Their molecular weights were determined by mass spectrometry (electrospray).

A. Gadolinium chelate of [1,4,7,10-tetraazocyclododecane]-1,4,7,10-tetra(2-glutaric)acid (sodium salt);

1. 30 g of sodium carbonate and then 78 g of ethyl 2-bromoglutarate prepared, for example, as described in Acta Chim. Acad. Sci. Hung 41(3) 331–6 (1964) are introduced into a solution of 25 g of 1,4,7,10-tetraazacyclododecane in 280 ml of acetonitrile; the medium is maintained at reflux for one day, during which further addition of twice 78 g of the bromo derivative with 30 g of sodium carbonate is carried out. The precipitate is filtered after cooling and the organic phase is washed with water and is then extracted with dilute aqueous hydrochloric acid solution. The aqueous phase is brought to about pH 3–4 and is then extracted with toluene.

The desired product is purified by chromatography on silica, eluting with methylene chloride, optionally mixed with acetone.

2. Hydrolysis of the ester groups:

46 g of the octaester dissolved in 52 ml of ethanol are introduced into 350 ml of water into which 50 g of NaOH pellets have been added.

After stirring for two days at 80° C., 500 ml of cationic exchange resin in weakly acidic form are introduced into the cooled solution in order to neutralize it, followed, after separating out the solid phase, by 500 ml of anionic exchange resin in strongly basic form. The resin is separated out and introduced into 500 ml of aqueous 6N acetic acid solution; the final product, passed into solution, is recovered as a powder by evaporating off the solvent under vacuum.

HPLC: 25 cm×4.6 mm column of Nucleosil® C18 100-5 silica gel.

Eluent No. 1: aqueous $H_2SO_4$ (0.1%) for 10 minutes and then with 0 to 10% (v/v) of $CH_3CN$ in 10 minutes: f=1 ml/min; T=25° C.;

$t_r$=5.4; 8.7; 10.2; 14 min (isomers) ($CH_3COOH$–$t_r$=4.5 minutes).

3. Complexation:

With gadolinium oxide: 0.47 g of gadolinium oxide is introduced into 30 ml of a solution of 2 g of the above octaacid at a pH of from 5.5 to 6, and the mixture is maintained at 80° C. for 3 hours, during which the pH is adjusted if necessary. After cooling, at pH=6.5, 2 g of Chelex® 100 resin, sold by Sigma in $Na^+$ form, are introduced; after a few hours of contact, the resin is separated out and the solution is poured into 10 volumes of ethanol in order to precipitate the chelate.

With gadolinium chloride: a mixture of 6.5 g of the octaacid and 3.5 g of $GdCl_3.6H_2O$ in 130 ml of water is brought to pH 6.5 by addition of aqueous NaOH (1N) and this mixture is maintained at 60° C. for 2 hours, during which the pH is maintained at 6.5 by addition of 21 ml in total of aqueous 1N NaOH. After a few hours at room temperature, the mixture is concentrated to 25 ml and the final product is precipitated from 10 volumes of $C_2H_5OH$.

B. Gadolinium chelate of 1,4,7,10-tetraazacyclododecane-1,4,7-tri(2-glutaric) acid (formula II;

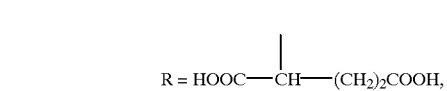

R'=H, M=Gd):

1. 10-Benzyl-1,4,7,10-tetraazacyclododecane:

30.5 g of benzyl chloride are introduced dropwise into a solution of 50 g of 1,4,7,10-tetraazacyclododecane in 500 ml of chloroform. After stirring for 24 hours at room temperature, the reaction medium is filtered; the filtrate is concentrated to dryness. The residue is taken up in 350 ml of water and 75 ml of toluene and, after decantation and separation of the toluene phase, the aqueous phase is then extracted with twice 200 ml of dichloromethane. The organic phase is dried over sodium sulphate and then concentrated to dryness. 21 g of the product in oily form are obtained.

2. 10-Benzyl-1,4,7,10-tetraazacyclododecane-1,4,7-tri (methyl 2-glutarate):

A solution of 56.3 g of methyl 2-bromoglutarate in 50 ml of acetonitrile is introduced dropwise into a suspension of 18.7 g of the above product with 24.7 g of sodium carbonate in 300 ml of acetonitrile. The reaction medium is maintained at reflux for 36 hours; after filtration at room temperature, the solvent is removed by evaporation and the residue is dissolved in the minimum amount of ethyl acetate and purified by chromatography on a column of silica, eluting with a mixture of ethyl acetate and petroleum ether (40/60 to 70/30 v/v). 20.7 g of the product are thus obtained in the form of an oil.

3. 10-Benzyl-[1,4,7,10-tetraazacyclododecane]-1,4,7-tri (2-glutaric) acid:

16.7 g of the oil obtained above dissolved in 40 ml of methanol are introduced into 125 ml of water into which 25 g of NaOH have been dissolved; the mixture is kept stirring at 70° C. for 48 hours. The methanol is then removed under reduced pressure, 400 ml of cation-exchange resin in weakly acidic form (Amberlite®—IRC 50 sold by Rohm & Haas) are then introduced, followed, after separation, by anion-exchange resin in strongly basic form (Amberlite®—IRA 458), the expected product being bound to the anionic resin. It is recovered by elution with 2 liters of aqueous 3N acetic acid solution, followed by 2 liters of 6N solution.

After removing the solvents, 13.5 g of white crystals are obtained, as a mixture of isomers.

HPLC: column No. 1: 25 cm×4 mm Lichrospher® 100-RP18–5 µm. (Merck, Germany);

Eluent No. 1

$t_r$=28, 30 minutes (2 isomer multiplets, 75/25 by area).

4. 1,4,7,10-Tetraazacyclododecane-1,4,7-tri(2-glutaric) acid:

13 g of the above compound dissolved in 210 ml of water and 90 ml of methanol are hydrogenated for 3 hours at room temperature at a pressure of $28 \times 10^4$ Pa in the presence of 10% palladium on charcoal containing 50% water. After removing the catalyst and the solvents by evaporation, 11 g of white powder are obtained.

HPLC: column No. 1; eluent No. 1.

$t_r$=8, 9 minutes (2 isomer multiplets, 75/25 by area).

5. Complexation:

A solution of 1.6 g of the above compound and 1 g of $GdCl_3.6H_2O$ in 30 ml of water at 60° C. is maintained at pH 5 by addition of aqueous 3N NaOH for 4 hours. The solution is concentrated to a volume of 10 ml and the residue is precipitated from 100 ml of ethanol. 1.6 g of the expected gadolinium complex are recovered by filtration.

HPLC: column No. 1; eluent No. 1; $t_r$=24, 26 minutes.

C. Gadolinium chelate of 1,4,7,10-tetraazacyclododecane-1,4,7-tri(2-glutaric)-10-acetic acid:

1. 1 g of the acid obtained in step 4 of preparation B are dissolved in 8 ml of water with 270 mg of bromoacetic acid and the mixture is maintained for 3 hours at 70° C. at pH 10 controlled by addition of aqueous 1N NaOH. 100 ml of water and 10 ml of Amberlite® IRC 50 resin are then added at room temperature; after contact for one hour, the resin is separated out and 50 ml of Amberlite® IRA 458 resin are introduced into the medium. After 12 hours, the resin is separated out and introduced into a column. The desired product is extracted therefrom by elution with 500 ml of aqueous 1N acetic acid solution. 0.8 g of white crystals is thus obtained.

HPLC: column No. 2: 25 cm×4 mm Symmetry®—RP 18–5 µm (Waters);

Eluent No. 1; $t_r$=4 minutes.

2. Complexation:

0.45 g of $GdCl_3.6H_2O$ and 0.75 g of the above compound are introduced into 13 ml of water; the pH is brought to 6 by addition of aqueous NaOH solution (1N); the reaction medium is then maintained at 60° C. for 5 hours, during which the pH is adjusted several times by addition of NaOH solution. After cooling, the medium is introduced into 130 ml of ethanol and the precipitate is recovered to give 0.75 g of chelate.

D. N,N'-(2,3,4,5-Tetrahydroxypentyl)-N,N'-[2-(hydroxyethoxy)ethyl]-2,4,6-triiodo-5-(glycylamino) isophthalamide:

1. 5-[2-(Hydroxyethoxy)ethylamino]pentane-1,2,3,4-tetraol:

84 g of 2-aminoethoxyethanol and 150 g of D-xylose are dissolved in 2.5 l of methanol; the mixture is hydrogenated at room temperature at a pressure of $6 \times 10^5$ Pa, in the presence of 50 g of 10% palladium on charcoal. The catalyst is removed by filtration and the solvent is distilled off. The residue, dissolved in the minimum amount of water, is chromatographed on 100 ml of Amberlite® IRN 77 resin ($H^+$), eluting with aqueous $NH_4OH$ solution, and then on 1 kg of Geduran® SI60 silica gel to give 170 g of amino alcohol in the form of a brown oil.

TLC: $CH_3OH/NH_4OH$ at 25%–(7/3–v/v)–$R_f$=0.3.

$^{13}C$ NMR: (DMSO- d6–50.3 MHz); δ (ppm): 51.4, 48.9 (2×$CH_2NH$); 62.9; 60.5 (2×$CH_2OH$); 71.9; 71.2; 70.6 (3×CHOH); 72.3; 69.7 ($CH_2OCH_2$).

The arabinose or ribose derivative can be prepared in the same way.

2. N,N'-(2,3,4,5-Tetrahydroxypentyl)-N,N'-[2-(hydroxyethoxy)ethyl]-2,4,6-triiodo-5-(phthalamidoacetamido)isophthalamide:

30 g of the amino alcohol prepared above are dissolved in 100 ml of dimethylacetamide at 45° C., 22 g of the substituted isophthalic acid dichloride and 12 g of triethylamine are then introduced and the medium is left stirring at this temperature for 24 hours. The precipitate formed is recovered at room temperature and the solvent is removed by distillation under vacuum.

The residue dissolved in 50 ml of water is eluted through 100 ml of Amberlite® IMAC HP 1110 resin ($H^+$); after concentration of the solution to 10 ml, the residue is poured into 1500 ml of isopropyl alcohol and the precipitate formed is recovered after 24 hours.

3. Release of the amine:

42 g of the product prepared above dissolved in 60 ml of water are introduced at 80° C. into a solution of 40 ml of water and 2.7 ml of hydrazine hydrate. After stirring for 5 hours at this temperature, the medium is filtered and then acidified to pH 1 by addition of concentrated hydrochloric acid. The precipitate formed is separated out and the filtrate is concentrated. The residue dissolved in 30 ml of water is chromatographed on 30 ml of Amberlite® IMAC HP 111E resin ($H^+$) and then on 55 ml of Amberlite® IRA 67 resin ($OH^-$). The concentrated eluate is bound to 350 ml of Amberlite® 252 Na resin ($H^+$), from which it is eluted with aqueous $NH_4OH$ solution (2N). w=20 g.

HPLC: column No. 1; Eluent No. 2: $H_2O/CF_3COOH$ (pH 3.4) with acetonitrile gradient from 95/5 to 50/50 v/v over 50 minutes;

$t_r$=10–20 minutes (mixture of isomers).

E. N,N'-[bis(2,3,4,5,6-Pentahydroxyhexyl)]-2,4,6-tribromo-5-(glycylamino)isophthalimide:

1. 5-Amino-2,4,6-tribromoisophthalic acid:

156 g of bromine are introduced slowly into 300 ml of an aqueous solution of 50 g of 5-aminoisophthalic acid and 55 ml of 37% hydrochloric acid. After stirring overnight, the excess bromine is neutralized by addition of aqueous sodium bisulphite solution and the precipitate is then recovered. Yield: 90%.

2. 5-(Phthalimidoacetamido)-2,4,6-tribromoisophthalic acid:

27 ml of thionyl chloride are introduced slowly into a solution of 69 g of N-phthaloylglycine in 200 ml of dimethylacetamide at 10° C. and, after stirring for 2 hours, 100 g of the acid obtained above are introduced at about 15–20° C. After leaving overnight at room temperature, the mixture is poured into 800 ml of hot water. 140 g of final product are thus recovered.

3. Chloride of the above diacid:

70 ml of thionyl chloride are introduced slowly, at 18° C., into a solution of 100 g of the diacid in 300 ml of dioxane and 50 ml of dimethylformamide. The yellow precipitate formed after stirring for 3 days at room temperature is filtered off and washed with methyl t-butyl ether. 70 g of beige solid are thus obtained.

4. N,N'-[bis(2,3,4,5,6-Pentahydroxyhexyl)]-2,4,6-tribromo-5-(phthalimidoacetamido)isophthalamide:

150 g of disorbitylamine are dissolved in 600 ml of N-methylpyrrolidone at 80° C. and 16 g of dry sodium carbonate are introduced into the medium at 60° C., followed by 96 g of the above acid chloride. After stirring for one hour at this temperature and 16 hours at room temperature, the precipitate is removed and the solution is poured into 1.6 l of isopropanol. The precipitate recovered weighs 200 g.

5. Hydrazinolysis:

200 g of the above product and 17 ml of hydrazine hydrate are introduced into 400 ml of water at 70° C. After stirring for 3 hours, the mixture is acidified to pH 4 by addition of 6N hydrochloric acid at room temperature. The precipitate formed is then removed and the filtrate is neutralized by addition of aqueous 1N NaOH solution. The excess hydrazine is removed by reverse osmosis. The residual solution is treated with 10 ml of strong cationic resin and then 65 ml of weak anionic resin.

The final product is then extracted from the solution by binding it to a strong cationic resin in $H^+$ form, from which it is eluted with a dilute aqueous NaCl solution (0.1 M). w=80 g.

HPLC: column No. 1; Eluent No. 2; $t_r$=about 7 minutes.

F. N,N'-[bis(2,3,4,5,6-Pentahydroxyhexyl)]-2,4,6-triiodo-5-(glycylamino)isophthalimide:

1. 5-(Phthalimidoacetamido)-2,4,6-triiodoisophthaloyl chloride:

149 ml of $SOCl_2$ are introduced into a solution of 335 g of N-phthaloylglycine in 1 l of N-methylpyrrolidone at 10° C., followed, after 3 hours, by 700 g of 2,4,6-triiodo-5-aminoisophthaloyl dichloride. After stirring for 3 days at room temperature, the medium is poured into 4.5 l of 2/1 v/v aqueous ethanol). The pH is brought to 5 by addition of triethylamine, after which the precipitate formed is recovered and can be purified by washing with isopropanol. w=850 g.

2. Amidification with disorbitylamine H—N[CH$_2$(CHOH)$_4$CH$_2$OH]$_2$:

Working as for the analogous tribromo compound, the product is obtained in a yield of 85%.

3. Hydrazinolysis:

420 g of the above triiodophthalimide dissolved in 1 l of water and 300 ml of hydrazine hydrate are maintained for several hours at 80° C. After acidifying the medium to pH 3.6, the excess hydrazine is removed by chromatography on a cation-exchange resin ($H^+$) such as IMAC® HP111E sold by Rohm & Haas, and the excess chlorides are removed with an anion-exchange resin ($OH^-$).

The final product can be purified by chromatography on cation-exchange resin (strong $H^+$) and precipitated from its aqueous solution in ethanol. 50% yield.

HPLC: column No. 1;
Eluent No. 4: $CH_3CN/P.I.C.$® B8 (0.05 M) (Waters) 15/85; flow rate 1 ml/min.
$t_r$=3 minutes.

G. 1-Deoxy-1-[(2,3-dihydroxypropyl)amino]-D-galactitol

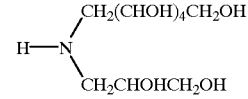

27 g of 3-aminopropane-1,2-diol and 50 g of D-galactose in 140 ml of methanol are kept stirring at 40° C. for 16 hours. 60 ml of water are then added and the imine is hydrogenated, in the presence of 7 g of palladium on charcoal (at 10%), for 7 hours at 60° C. and at a pressure of $20\times10^5$ Pa of hydrogen.

The catalyst is then separated out by filtration through Celite®. After removing the solvent under reduced pressure, the residue, dissolved in the minimum amount of water (50 ml), is introduced slowly into 600 ml of isopropanol. The precipitate formed is recovered. m.p.=132° C., 90% yield.

Before the precipitation from isopropanol, the crude product, dissolved in 200 ml of water, can also be chromatographed on 500 ml of an ion-exchange resin in sulphonic acid form, eluting with dilute aqueous $NH_4OH$ solution.

Under these conditions, the amino alcohol is a isomers (about 50/50) mixture of the two diastereoisomers.

The mixture can be enriched in one or other of the isomers by recrystallization, fractional precipitation or placing in suspension.

Thus, by treatment with refluxing methanol (25 g of amino alcohol in 500 ml of solvent), a mixture is obtained which contains an excess of one of the isomers: 65% of the isomer having the longer retention time, based on the areas measured on the chromatograms obtained under the following conditions:

Gas chromatography (derivative totally trifluoroacetylated by the reaction of trifluoroacetic anhydride at 60° C.).

Machine: Varian Star 3400;
Column: DB 1701 from J & W (0.25 μm–30 m×0.25 mm);
Carrier gas He–T injector (1/40 split)=290° C.;
T column=150° C. to 280° C. (5° C./min)–Volume: 1 μl;
$t_r$: 14.5 and 14.9 minutes (5.6 min for the starting aminopropanediol).

C NMR (200 MHz–DMSO d6–Ref DMSO–T=30° C.) δ (ppm): 71.7; 71.6; 70.5; 70.1; 69.5; 68.5; 68.2–(CHOH) 64.6; 63.2; ($CH_2OH$)–53.4; 53; 52.9 ($NCH_2$).

Each diastereoisomer can also be obtained by coupling D-galactose with the pure enantiomer of the aminopropanediol or by the reaction of the enantiomers of glycidol on N-(2,3,4,5,6-pentahydroxyhexyl)benzylamide as follows:

a) N-Benzyl-N-(2,3,4,5,6-pentahydroxyhexyl)amine:

29 g of D-galactose and 17 ml of benzylamine are dissolved in 230 ml of methanol and, after addition of 5 g of 5% palladium on charcoal, the mixture is maintained at 50° C. for 7 hours under a hydrogen pressure of $8\times10^5$ Pa.

After hydrogenation, aqueous hydrochloric acid solution is introduced into the reaction medium at 40° C. until the pH is acidic.

The mixture is filtered through Celite® at room temperature in order to remove the catalyst and, after partially concentrating, aqueous 5N NaOH solution is added until the pH is basic. The precipitate formed is recovered and recrystallized from ethanol.

$^{13}$C NMR (200 MHz–DMSO d6–Ref DMSO–T=30° C.) δ (ppm): 140.8 (C CH$_2$N)–128.8; 128.4; 126.9 (phenyl)–72; 70.6; 69.9; 68.8; (CHOH)–63.2 (CH$_2$OH)–53.1; 52.4 (CH$_2$NH).

b) N-Benzyl-N-(2,3-dihydroxypropyl)(2,3,4,5,6-pentahydroxyhexyl)amine:

6.5 g of the secondary amine obtained in the above step are dissolved in 200 ml of methanol at 60° C., 2.5 g of glycidol (racemic mixture or pure enantiomer) are then added to the solution at this temperature and the mixture is kept stirring for 24 hours. The solvent is then removed by distillation under reduced pressure and, after dissolving the residue in 200 ml of water, this solution is chromatographed on a column of Amberlite® IMAC 110 resin in H$^+$ form, eluting with dilute aqueous NH$_4$OH solution (0.1%). 5.5 g of the amine are thus obtained.

c) N-(2,3-Dihydroxypropyl)-N-(2,3,4,5,6-pentahydroxyhexyl)amine:

2 g of the tertiary amine obtained in the above step dissolved in 30 ml of water are hydrogenated at 45° C. under a hydrogen pressure of 100×10$^5$ Pa for 5 hours in the presence of 0.6 g of 10% palladium on charcoal. The solution is then filtered through Celite® to remove the catalyst and is concentrated under reduced pressure. The residue can be recrystallized from ethanol.

When coupled with (S)-glycidol, the amino alcohol diastereoisomer with the longer retention time under the conditions of the above gas chromatography is obtained.

2. Reduction of the enamine:

7 g of sodium cyanoborohydride are introduced portionwise, with stirring, into a solution of 19 g of the solid in 500 ml of acetonitrile and 50 ml of acetic acid, and the mixture is kept stirring overnight at room temperature. After removing the solvent under reduced pressure, the oily residue is dissolved in a dichloromethane/methanol mixture (99/1) and filtered through silica. After evaporating off the solvent, 19 g of yellow oil are recovered.

3. Debenzylation:

8 g of the octaester obtained, in a water/methanol mixture (175 ml/75 ml), are hydrogenated for 6 hours in the presence of 4 g of 10% palladium on charcoal (pressure: 3.5×10 Pa). After separating out the catalyst by filtration and removing the solvent by distillation, 3 g of octaacid are obtained in the form of a white powder.

HPLC: Column No. 1; Eluent No. 1; $t_r$=18 to 19 minutes.

4. Complexation:

1 g of the octaacid obtained is suspended in 20 ml of water, the pH is brought to 5.5 by addition of aqueous 1N NaOH solution and 0.285 g of Gd$_2$O$_3$ is added. After the reaction medium, whose pH is maintained between 5.5 and 6.5 by addition of aqueous 1N HCl solution, has been stirred for 4 hours at 70° C., it is filtered and the filtrate is concentrated to dryness to give the sodium salt of the chelate.

EXAMPLE 1

Gadolinium chelate of formula I in which

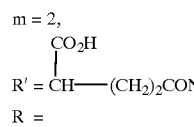
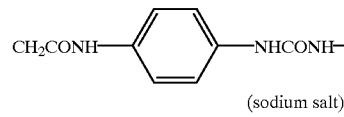
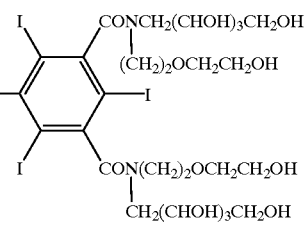

(sodium salt)

Starting with D-glucose and D-mannose and by applying these processes, diastereoisomers of these amino alcohols will be obtained, whereas other amino alcohols may be obtained starting with different amino alcohols or with different sugars.

H. Gadolinium chelate of (1,4,7,10-tetraazacyclododecane)-1,4,7,10-tetra(2-succinic) acid:

1. Coupling of benzyl acetylenedicarboxylate with the 4 nitrogen atoms of cyclen:

23 g of benzyl acetylenebicarboxylate, prepared as described in J. C. S. Perkin I, p. 2024–2029, (1973), dissolved in 25 ml of acetonitrile, are added dropwise, at 20° C., to a solution of 2.7 g of cyclen in 50 ml of acetonitrile. After stirring for 3 hours at 50° C., the solvent is removed under reduced pressure and the residue is purified by chromatography on silica, eluting with a dichloromethane/methanol mixture (98/2–v/v) to recover 19 g of yellow solid.

1. 4-[N'-(4-Nitrophenyl)ureido]benzoic acid:

24.6 g of 4-nitrophenyl isocyanate are introduced, with stirring at 10° C., into 80 ml of tetrahydrofuran, followed by slow introduction of 20.5 g of 4-aminobenzoic acid dissolved in 70 ml of tetrahydrofuran. The mixture is allowed to warm to room temperature and stirring is continued for 1 hour, after which the precipitate formed is recovered. w=45 g.

HPLC: Column No. 1; Eluent No. 2; H$_2$O/CF$_3$COOH; pH=3.4 with acetonitrile gradient (95/5 to 50/50–v/v over 50 min); flow rate 1 ml/min; $t_r$=44 minutes.

2. 4-[N'-(4-Aminophenyl)ureido]benzoic acid:

22 g of the above product and 37 ml of aqueous 1N NaOH solution are introduced into 280 ml of water with 3 g of palladium on charcoal (5%). The medium is maintained at a hydrogen pressure of 0.6 MPa for 6 hours at 65° C. After cooling to room temperature, the pH is brought to 10 and the catalyst is filtered off on Celite®, after which the filtrate is acidified to pH 5.3 by addition of aqueous 6N HCl solution; the precipitate obtained is washed with acetone. w=13.2 g.

HPLC: Column No. 1; Eluent No. 2; $t_r$=33 minutes.

3. 4-[N'-[4-(Phthalimidoacetamido)phenyl]-ureido] benzoic acid:

5.8 g of phthalimidoacetic acid are dissolved in 26 ml of dimethylacetamide at 10° C. and 2 ml of thionyl chloride are introduced, while maintaining the temperature, followed, after stirring for 2 hours, by addition of 7 g of the compound obtained in the above step.

After 12 hours at room temperature, the reaction medium is poured into 250 ml of water and the precipitate formed is washed with water at 25° C. and then at 95° C., until neutral. w=10.4 g.

HPLC: Column No. 1; Eluent No. 2; $t_r$=40 minutes.

4. N,N'-(2,3,4,5-Tetrahydroxypentyl)-N,N'-[2-(hydroxyethoxy)ethyl]-2,4,6-triiodo-5-[4-[N'-(4-phthalimidoacetamidophenyl)ureido]benzoylglycylamino] isophthalamide:

4 g of the compound obtained above are dissolved in 40 ml of dimethylacetamide with 1.7 g of HOBT.H$_2$O and 9.3 g of N,N'-bis(2,3,4,5-tetrahydroxypentyl)-N,N'-bis(hydroxyethoxyethyl)-2,4,6-triiodo-5-(glycylamino) isophthalamide, followed by 2.4 g of EDCI.HCl at 0° C. After stirring overnight at room temperature, the medium is poured into 300 ml of dichloromethane. The precipitate recovered is washed with diethyl ether.

HPLC: Column No. 1; Eluent No. 2; $t_r$=30–33 minutes (mixture of isomers).

5. Removal of the phthalimido group: product of formula III in which Z=CH$_2$CONH; Z'=NHCONH; Z"=CONHCH$_2$CONH;

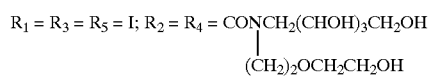

11.5 g of the above compound are introduced into 45 ml of water at 80° C., followed by 1.12 ml of hydrazine hydrate (0.023 mol). After 2 hours 45 min at 80° C., the mixture is cooled to 0° C. and acidified to pH 1 by addition of aqueous 12N HCl. The mixture is then filtered through Celite® at room temperature and then filtered through 16 ml of IMAC® HP111E cationic resin (H$^+$) and 80 ml of IMAC® HP661 weak anionic resin (OH$^-$), sold by Rohm & Haas.

After a final purification by filtration on silanized silica, 4.6 g of the final product are obtained.

HPLC: Column No. 1; Eluent No. 2; $t_r$=24–27 minutes (mixture of isomers).

6. Coupling of the products A and III 0.057 g of NHS (sodium salt) and 0.76 g of EDCI.HCl are introduced at 40° C. into 20 ml of an aqueous solution, at pH 6, of 4.5 g of the above amine and 0.63 g of the chelate A prepared according to (A). After 15 minutes, the mixture is poured into water and the precipitate is recovered. After removal of the starting materials, the compound of formula I is obtained.

Steric exclusion chromatography (SEC).

Conditions No. 1: carried out on a series of 4 columns (30 cm×8 mm) sold by Shodex (JP) under the references OH Pak SB-HQ, containing polyhydroxymethacrylate gel, the exclusion limits of which, determined with pullulan, are successively 10$^6$ Kdaltons (SB-804) 10$^5$ Kdaltons (SB-803); 10$^4$ Kdaltons (SB-802-5); 10$^4$ Kdaltons (SB-802-5).

Eluent: aqueous NaCl (0.16 M)/acetonitrile (70/30–v/v); flow rate 0.8 ml/min.

T=30° C.; $t_r$: 38 minutes (50–53 min for the starting amine).

HPLC: Column No. 3, 25 cm×4.6 mm Platinum EPS C18 100 Å; 5 µM (Alltech);

Eluent No. 3: water/CH$_3$CN from 98/2 to 60/40–v/v in 50 min; flow rate: 1 ml/min;

T=25° C.; $t_r$=26 minutes.

EXAMPLE 2

Gadolinium chelate of formula I in which m=2

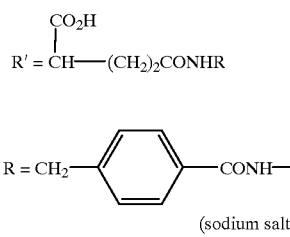

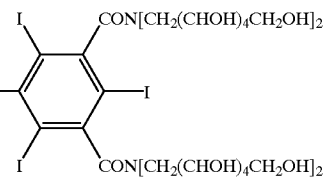

1. 4-[4-(Phthalimidomethyl)benzamido]-benzoic acid:

37 g of N-carbethoxyphthalimide are introduced into a solution prepared with 25 g of 4-aminomethylbenzoic acid, 18 g of Na$_2$CO$_3$ and 165 ml of water. The precipitate formed is recovered and is then suspended in 60 ml of dimethylacetamide, into which 4.7 ml of thionyl chloride are introduced slowly at 10° C. After 3 hours at this temperature, 9 g of 4-aminobenzoic acid are introduced and the medium is maintained for 12 hours at room temperature and then poured into 600 ml of water. The precipitate formed is recovered.

HPLC: Column No. 1; Eluent No. 2; $t_r$=48 minutes.

2. N,N'-bis(2,3,4,5,6-Pentahydroxyhexyl)-2,4,6-triiodo-5-[4-(4-aminomethylbenzamido)benzoylglycylamino] isophthalamide:

a) 160 ml of dimethylacetamide are stirred with 39 g of 5-glycylamino-N,N'-bis(2,3,4,5,6-pentahydroxyhexyl)-2,4, 6-triiodoisophthalamide, 4.6 ml of triethylamine, 5.7 g of HOBT.H$_2$O and 12 g of the product obtained above, until dissolved, after which the solution is cooled to 0° C. and 8 g of EDCI.HCl are added. At the end of the reaction, the medium is poured into 1000 ml of dichloromethane. The recovered precipitate is purified by precipitation in methanol from its aqueous solution. w=43 g.

b) Hydrazinolysis 25 g of the phthalimide obtained above are dissolved in 50 ml of water at 80° C., after which 2.2 ml of hydrazine hydrate are added. After stirring for 3 hours, the medium is cooled and acidified to pH 1 by addition of 12N HCl. The medium is then filtered through Celite® and then purified by chromatography on weak cationic resin (H$^+$) and then on weak anionic resin (OH$^-$).

15 g of the desired product are thus recovered.

HPLC: Column No. 1; Eluent No. 2; t$_r$=19 minutes.

c) Coupling with the gadolinium chelate A:

15 g of the amine thus obtained and 1.9 g of the chelate A (sodium salt) are dissolved in 40 ml of water. After acidification to pH 6 by addition of aqueous 1N HCl, 2.3 g of EDCI.HCl are introduced at 40° C. After stirring for 2 hours, the medium is introduced into 400 ml of ethanol; the precipitate formed, dissolved in water, is filtered through Norit® carbon black. 8.5 g of pure product are thus obtained.

SEC: conditions No. 1; t$_r$=36 minutes.

HPLC: Column and eluent No. 3; t$_r$=23 minutes.

EXAMPLE 3

Gadolinium chelate of formula I in which the catalyst. The precipitate formed during the acidification of the filtrate to pH 5.3 is recovered and dried. w=106 g; F>260° C.

c) 4-[4-(Phthalimidoacetamido)benzamido]benzoic acid:

32 ml of thionyl chloride are introduced dropwise into a solution of 90 g of phthalimidoacetic acid in 400 ml of dimethylacetamide at 10° C., followed, after stirring for 3 hours, by addition of 105 g of the amino acid obtained above, at a temperature below 20° C.

After stirring for 12 hours, the medium is poured into 4 liters of water and the precipitate is recovered and washed with hot water. Weight after drying: 176 g. m.p.>260° C.

d) Chloride of the above acid:

2.5 ml of thionyl chloride are introduced into 10 g of the acid suspended in 50 ml of dioxane and 1 ml of dimethylformamide, and the mixture is kept stirring at 50° C. for 5 hours.

After addition of one volume of diisopropyl ether, 10 g of precipitate are recovered.

The acid can also be suspended in toluene with tricaprylylmethylammonium chloride as catalyst.

e) N,N'-bis(2,3,4,5,6-Pentahydroxyhexyl)-2,4,6-tribromo-5-(4-[4-(phthalimidoacetamido)benzamido]benzoylglycylamino)isophthalamide:

A solution of 2.25 g of the acid chloride with 5 g of N,N'-bis(2,3,4,5,6-pentahydroxyhexyl)-2,4,6-tribromo-5-(glycylamino)isophthalamide and 0.7 ml of triethylamine in 25 ml of dimethylacetamide or N-methylpyrrolidone is kept stirring for 12 hours and then poured into 60 ml of ethanol. 6.2 g of precipitate are thus recovered.

HPLC: Column No. 1: Eluent No. 2; t$_r$=27–35 min (mixture of isomers).

m = 2

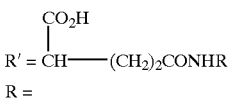

R =

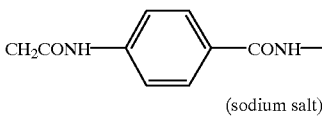 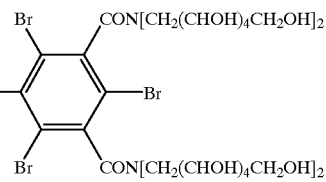

(sodium salt)

a) 4-[4-Nitrobenzamido} benzoic acid:

100 g of 4-nitrobenzoyl chloride are introduced portionwise into 74 g of 4-aminobenzoic acid and 360 ml of dimethylacetamide, while maintaining the temperature at less than 25° C. After stirring for 24 hours, 500 ml of methylene chloride are added, at 10° C., in order to precipitate the expected product. After washing with water and drying, 145 g of product are recovered.

b) 4-(4-Aminobenzamido)benzoic acid:

A suspension of 136 g of the above acid in 1.8 liters of water, to which 240 ml of aqueous 1N NaOH solution and 14 g of palladium on charcoal (10%) have been added, is maintained under a hydrogen pressure of 0.6 MPa for 4 hours.

The pH of the final suspension is then brought to about 10, after which the mixture is filtered through Celite® to remove f) Hydrazinolysis:

A solution of 0.6 ml of hydrazine hydrate in 10 ml of water is introduced into a solution of 10 g of the above phthalimide in 40 ml of dimethylacetamide at 80° C. After stirring for 3 hours at this temperature, the cooled mixture is poured into 125 ml of ethanol. 9 g of precipitate are recovered and are purified by treatment of their aqueous solution with a strong anionic resin (OH$^-$) and then a weak cationic resin (H$^+$). w=8 g.

The reaction medium can also be acidified in order to separate out the precipitated phthalylhydrazide and to remove the solvent and the molecules of low weight by ultrafiltration, before a final precipitation in aqueous ethanol.

HPLC: Column No. 1; eluent No. 2 but 90/10 v/v without gradient; t$_r$=28–35 min.

g) Coupling with the chelate A to obtain the compound of formula I:

5 g of the compound obtained in step (f) are dissolved in 135 ml of water with 0.65 g of the chelate A (sodium salt); the pH of the medium is lowered to 6 by addition of aqueous 1N HCl, after which 0.8 g of EDCI.HCl are introduced into the medium at 40° C. After stirring for 2 hours and cooling to room temperature, the medium is poured into 135 ml of ethanol.

1.6 g of the chelate A (sodium salt) can also be introduced into 25 ml of aqueous solution of 10 g of the amine obtained in f, followed successively, at pH 6.5, by 18 ml of dioxane, 1.4 g of EDCI and 0.08 g of HOBT. After 2 hours at room temperature, the reaction medium is poured into 100 ml of ethanol and the precipitate is recovered. After redissolving in 100 ml of water it is treated twice with 1 g of carbon black and then reprecipitated in 3 volumes of ethanol.

The precipitate formed is purified by treatment with 5 ml of Chelex 100 ion-exchange resin (Na$^+$) sold by Sigma, and then by dia-ultrafiltration on a membrane with a cutoff threshold of 5 KD, at pH 7. W=4 g.

SEC: Conditions No. 1; $t_r$=34 minutes.

HPLC: Column and eluent No. 3; $t_r$=23 minutes.

EXAMPLE 4

Gadolinium chelate of formula I in which m = 2
R' = H et R =

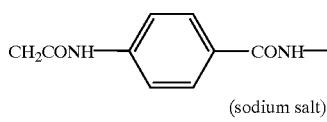
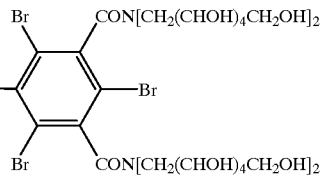

0.3 g of the gadolinium complex of 1,4,7,10-tetraazacyclododecane-1,4,7-triglutaric acid prepared according to (B), 2 g of the amine prepared in Example 3 (f) and 0.3 g of EDCI.HCl in 5 ml of water are kept stirring for 5 hours at 40° C., while maintaining the pH at 7 by addition of aqueous 1N HCl solution. The medium is poured into 50 ml of ethanol and the precipitate formed is recovered. It is purified in solution in 120 ml of water by ultrafiltration on a membrane with a cutoff threshold of 3 KD, to remove the unreacted starting materials. After stirring on carbon black and filtration, the solution is brought to dryness to give 1 g of white solid.

SEC: Conditions No. 1; $t_r$=36.8 minutes.

HPLC: Column and eluent No. 3; $t_r$=31 minutes.

EXAMPLE 5

Gadolinium chelate of formula I in which m=2 R'=CH$_2$COOH and R=

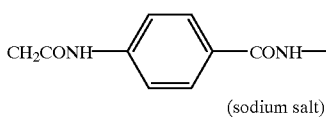
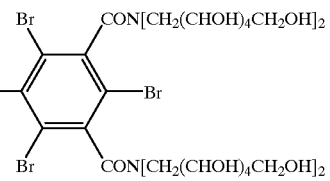

By applying the same procedure as in Example 4, 0.8 g of final product is obtained from 0.3 g of starting chelate C and 2 g of the amine prepared in Example 3f.

SEC: Conditions No. 1; $t_r$=35.7 minutes

HPLC: Column and eluent No. 3; $t_r$=22 minutes.

EXAMPLE 6

Gadolinium chelate of formula I in which m=2

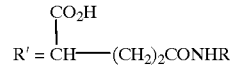

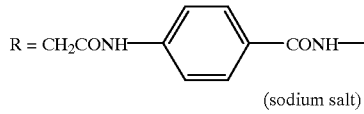 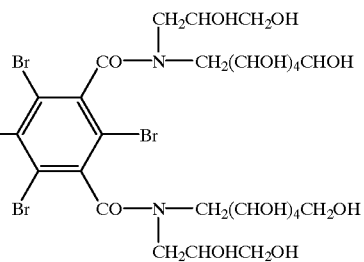

(sodium salt)

1. 5-[4-(4-Aminobenzamido)benzamido]-2,4,6-tribromoisophthalic acid:

(a) 4-(4-Nitrobenzamido)benzoyl chloride:

70 g of the acid are refluxed for 8 hours in 250 ml of thionyl chloride and 0.1 ml of dimethylformamide. The excess thionyl chloride is distilled off under reduced pressure and the residue is poured into 1.5 l of ethyl acetate and 500 g of crushed ice with stirring.

The final product is extracted into the organic phase, which is washed with water, with aqueous sodium bicarbonate solution and then dried and concentrated. w=64 g.

(b) 5-[4-(4-Nitrobenzamido)benzamido]-2,4,6-tribromoisophthalic acid:

A solution of 64 g of the acid chloride with 67 g of 5-amino-2,4,6-tribromoisophthalic acid in 170 ml of dioxane is refluxed for 18 hours. The solvent is evaporated off and, after washing with 300 ml of hot ethyl acetate, the residue is dissolved in 600 ml of water with a sufficient amount of 5N NaOH to give a pH of 7; after washing with ethyl acetate and acidification, the expected product, which precipitates out, is recovered. w=73 g.

(c) Reduction:

19 g of the above product in aqueous solution at pH 6 are maintained for 7 hours under a hydrogen pressure of 0.5 MPa in the presence of 2 g of platinum on charcoal type 156 (Johnson Matthey). After filtration, the solution is evaporated. w=15 g.

2. N,N'-(2,3-Dihydroxypropyl)-N,N'-(2,3,4,5,6-pentahydroxyhexyl)-2,4,6-tribromo-5-[4-(4-glycylaminobenzamido)benzamido]isophthalimide:

(a) 13 g of the above derivative are introduced, at 10° C., into 10 ml of a solution of the phthalimidoacetyl chloride prepared, with 4.7 g of phthaloylglycine and 1.7 ml of SOCl$_2$. After stirring for 2 hours at 20° C., the solution is poured into 150 ml of water at 80° C. and the precipitate is recovered. w=10.6 g.

(b) Acid chloride:

16 ml of thionyl chloride are introduced into a solution of 12.4 g of the above derivative in 60 ml of dioxane and 10 ml of dimethylformamide, while keeping the temperature below 10° C. After stirring for 30 minutes, the solution is poured into 200 ml of water and the precipitate recovered is washed with 100 ml of ethyl acetate. w=12 g.

(c) Coupling with the amino alcohol:

11.6 g of the acid dichloride are introduced, at 60° C., into 120 ml of N-methylpyrrolidone containing 13.5 g of 1-deoxy-1-(2,3-dihydroxypropylamino)-D-galactitol prepared according to G. After stirring for 4 hours, the mixture is introduced into 1200 ml of dichloromethane and the precipitate is recovered. w=35 g.

(d) Removal of the phthalimido protecting group:

14 g of the above derivative are introduced into 30 ml of water at 80° C., containing 1.2 g of hydrazine hydrate. After 3 hours at this temperature, the solution is acidified to pH 1 by addition of aqueous 5N HCl solution. The precipitate formed after several hours is separated out and the filtrate is treated successively with the resins IMAC® HP 1110 Na and HP 661 (Rohm & Haas).

HPLC: Column No. 1; Eluent No. 2; $t_r$=25–28 minutes (starting material 32–36 minutes).

3. Reaction with the chelate A:

0.6 g of the gadolinium chelate A (Na salt), 0.7 g of EDCI.HCl and 4 g of the above amine are introduced in 15 ml of water; the pH is brought to 6 by addition of aqueous 1N HCl solution and the mixture is maintained at 40° C. for 2 hours and then introduced into 200 ml of ethanol. The precipitate formed is recovered and its solution in 100 ml of water is ultrafiltrated on a polyether sulphone membrane with a cutoff threshold of 5 KDa.

HPLC: Column and eluent No. 3; $t_r$=26 minutes.

SEC: Conditions No. 1; $t_r$=36 minutes.

EXAMPLE 7

Gadolinium chelate of formula I in which m=2

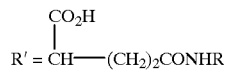

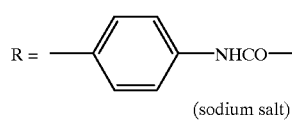 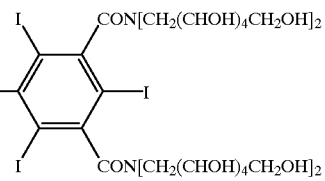

(sodium salt)

1. 4-(4-Aminophenylcarbamoyl)benzoic acid:

(a) Methyl 4-(4-nitrophenylcarbamoyl)benzoate:

10 ml of thionyl chloride are introduced portionwise, at about 10° C., into a solution of 25 g of terephthalic acid monomethyl ester in 125 ml of dimethylacetamide; after stirring for 1 hour 30 min at 15° C., the mixture is introduced slowly into a solution of 19 g of 4-nitroaniline in 125 ml of the same solvent. After 2 hours at 50° C., the precipitate formed is recovered.

Yield: 97%.

(b) Reduction:

10 g of the above nitro derivative are suspended in 100 ml of dimethylacetamide in the presence of 2.5 g of 10% palladium on charcoal (50% water) and maintained under a hydrogen pressure of 0.5 Mpa for 7 hours. The catalyst is removed by filtration of the medium through Clarcel® and the filtrate is introduced into 500 ml of water. The precipitate formed is recovered.

3. Coupling with the gadolinium chelate A:

0.125 g of the chelate (Na salt), 1.8 g of the above compound, 0.15 g of EDCI.HCl and 100 mg of sulphonic NHS are stirred for a few days at 40° C., while maintaining the pH at about 7 by addition of aqueous 1N HCl solution. The precipitate formed by introduction of 50 ml of ethanol is recovered and purified by ultrafiltration on a 5 kDa membrane, to give 1 g of the expected product.

SEC: Conditions No. 1; $t_r$=30 minutes.

HPLC: Column No. 3; Eluent No. 3; $t_r$=20 minutes.

EXAMPLE 8

Gadolinium chelate of formula I in which m=2

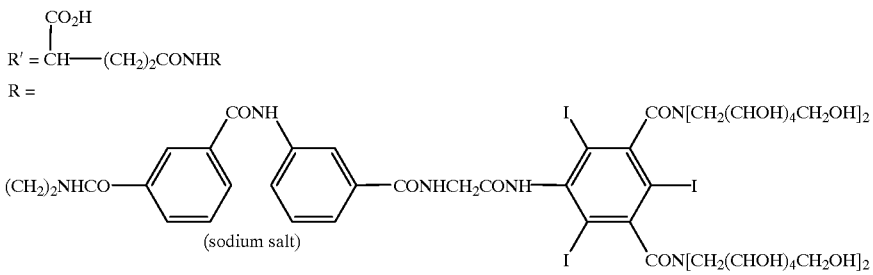

Yield: 97%.

(c) Hydrolysis of the ester group:

9 g of the above compound, 50 ml of aqueous NaOH (2N) and 25 ml of methanol are maintained at 60° C. for 2 hours. The solution is acidified, at 20° C., to pH 4.5 by addition of concentrated (37%) hydrochloric acid solution and 7 g of the precipitate formed are recovered.

HPLC: Column No. 1; Eluent No. 2; $t_r$=29 minutes.

2. N,N'-bis(2,3,4,5,6-Pentahydroxyhexyl)-5-[4-(4-aminophenylcarbamoyl)benzoylglycylamino]-2,4,6-triiodoisophthalamide:

25 g of the iodo aminoacetamidoisophthalamide prepared in F are stirred, for 2 hours at room temperature, with 3 ml of triethylamine, 5.8 g of the above product, 4.3 g of HOBT and 6 g of EDCI.HCl, and the mixture is then poured onto 700 ml of dichloromethane. The precipitate formed is recovered and purified by chromatography on a column of RP-2 silanized silica (Merck), eluting with water. 16 g of the expected product are recovered.

HPLC: Column No. 1; Eluent No. 2; $t_r$=14 minutes.

1. 3-[3-(Phthalimidoethylcarbamoyl)benzamido]-benzoic acid:

(a) 3-(Aminoethylcarbamoyl)benzoic acid:

A solution of 9 g of isophthalic acid monomethyl ester and 1.5 ml of ethylenediamine in 90 ml of methanol is stirred for 18 hours and then concentrated to dryness. The residue is washed with ice-cold methanol.

Yield: 91%

(b) Protection of the $NH_2$ as phthalimide:

9 g of the amine and 14 g of N-carbethoxyphthalimide are introduced into a solution of 6.9 g of sodium carbonate in 180 ml of water. After stirring for 1 h 30 min, the solid is recovered and the filtrate is acidified to pH 2. The phthalimide precipitates in the form of white crystals.

Yield: 80%.

HPLC: Column No. 1; Eluent No. 2; $t_r$=32 minutes.

(c) 2.6 ml of thionyl chloride are added drop-wise, at 10° C., to a solution of 12 g of the above phthalimide in 45 ml of dimethylacetamide. After 2 hours at 15° C., the orange-coloured solution is added slowly to a solution of 5 g of 3-aminobenzoic acid in 45 ml of dimethylacetamide. The reaction medium is maintained at 55° C. for 3 hours and then poured into 900 ml of water. The precipitate formed is recovered.

Yield: 96%.

2. N,N'-bis(2,3,4,5,6-Pentahydroxyhexyl)-5-[3-[3-(aminoethylcarbamoyl)benzamido]benzamidoacetamido]-2,4,6-triiodoisophthalamide:

(a) 20 g of the iodo aminoacetamiidoisophthalamide prepared according to F, 2.5 ml of triethylamine, 8.3 g of the above compound, 3.4 g of HOBT and 4.9 g of ECDI.HCl in 100 ml of dimethylacetamide are stirred for 1 hour 30 min. The reaction medium is then poured into 700 ml of dichloromethane and 26 g of the precipitate formed are recovered.

HPLC: Column No. 1; Eluent No. 2; $t_r$=26 minutes.

(b) Hydrazinolysis:

3.5 ml of hydrazine hydrate are introduced into a solution of 25 g of the above product in 55 ml of water at 80° C. After 8 hours at this temperature, the medium is acidified to pH 1 and the precipitate formed is recovered. It is purified by chromatography on cationic resin (H⁻) and then anionic resin (OH⁻). 70% yield.

HPLC: Column No. 1; Eluent No. 2; $t_r$=23 minutes.

3. Coupling with the gadolinium chelate A:

2 g of the chelate A (Na salt), 2.3 g of EDCI.HCl and 16 g of the above compound in 50 ml of water are maintained at pH 7 for 1 hour at 40° C. with stirring, after which 200 mg of sulphonic NHS are added and the stirring is continued at 40° C. for 3 hours. The medium is then poured into 500 ml of ethanol and the precipitate recovered is purified by ultrafiltration to give 10 g of the sodium salt of the expected product.

SEC: Conditions No. 1; $t_r$=36 minutes.

HPLC: Column No. 3; Eluent No. 3; $t_r$=21 minutes.

EXAMPLE 9

Gadolinium chelate of formula I in which m=2

1. 4-[4-(4-[Phthalimidomethyl]benzamido)benzamido]benzoic acid:

3.5 ml of thionyl chloride are introduced, at 15° C., into a solution of 19.3 g of 4-[4-[phthalimidomethyl]benzamido]benzoic acid, followed, after stirring for 2 hours 45 min, by 8 g of 4-aminobenzoic acid. After 12 hours at 20° C., the medium is poured into 500 ml of water. The precipitate formed is washed with dioxane. w=11.5 g.

HPLC: Column No. 1; Eluent No. 2; $t_r$=53 minutes.

2. N,N'-(2,3,4,5,6-Pentahydroxyhexyl)-N,N'-(2-hydroxyethyl)-4-[4-[4-(aminomethyl)benzamido]benzamido]benzamide:

(a) 4.8 g of 1-deoxy-1-(2-hydroxyethylamino)-D-glucitol, 4 g of HOBT.H₂O, 11 g of the above acid and 6.7 g of EDCI.HCl are stirred overnight at 20° C. The reaction medium is then poured into 500 ml of dichloromethane and the precipitate formed is washed with 300 ml of diethyl ether.

HPLC: Column No. 1; Eluent No. 2; $t_r$=39 minutes.

(b) Hydrazinolysis:

The above precipitate is introduced into 60 ml of dimethylacetamide and, at 80° C., 3.2 ml of hydrazine hydrate dissolved in 25 ml of water. After 3 hours, the medium is concentrated and the residue is dissolved in water. The aqueous phase is brought to pH 7.5 by addition of concentrated HCl solution and is then chromatographed on a strong cationic resin (H⁺) and then on a weak anionic resin (OH⁻). In ethanol, 3.5 g of precipitate are obtained.

HPLC: Column No. 1; Eluent No. 2; $t_r$=27 minutes.

3. Coupling with the gadolinium chelate A:

1.5 g of the above compound are brought to 40° C. with 0.5 g of the chelate A in 15 ml of water and 5 ml of dimethylacetamide, and 0.75 g of EDCI.HCl and 0.05 g of sulphonic NHS (sodium salt) are introduced. After stirring for 2 hours at this temperature, the reaction medium is poured into 2 volumes of ethanol and 1.3 g of precipitate are recovered.

HPLC: Column No. 3; Eluent No. 3; $t_r$=31 minutes.

EXAMPLE 10

Gadolinium chelate of formula I in which m=2

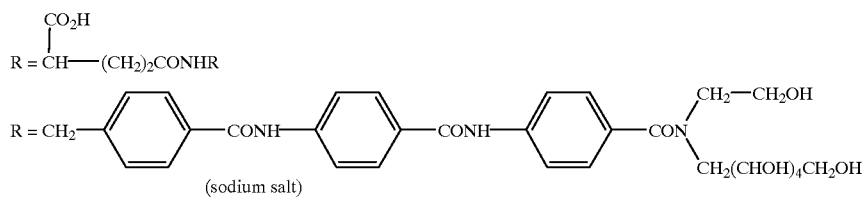

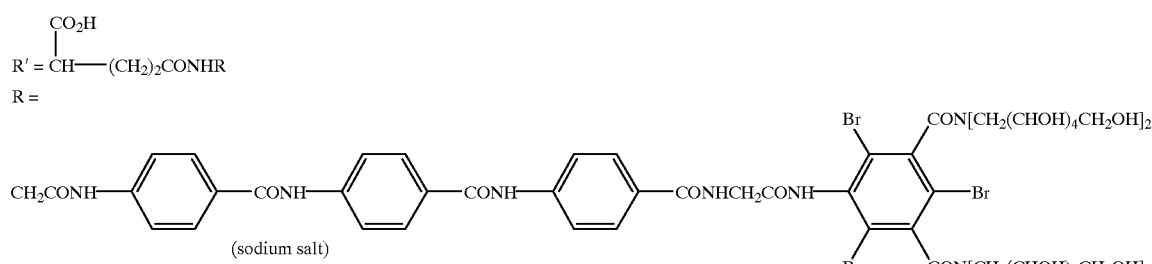

1. 4-[4-[4-Nitrobenzamido]benzamido]benzoic acid:

25.4 g of 4-nitrobenzoyl chloride are introduced into a solution, at 5° C., of 35 g of 4-(4-aminobenzamido)benzoic acid in 140 ml of dimethylacetamide. After stirring for one day at 20° C., the reaction medium is poured into 500 ml of dichloromethane. w=50 g.

2. Reduction of the nitro group:

A suspension of 13 g of the above acid in 400 ml of dimethylacetamide is hydrogenated at a pressure of 0.15 MPa for 4 hours in the presence of 3 g of 5% Pd/C (50% water). After filtration and evaporation of the solvent, 12 g of product are recovered.

3. 4-[4-[4-(Phthalimidoacetamido)benzamido]benzamido]benzoic acid:

A solution of 16.4 g of phthalimidoacetic acid in 40 ml of thionyl chloride is refluxed for 4 hours. After concentration, the reaction medium is introduced into 100 ml of diisopropyl ether. 10 g of acid chloride precipitate are recovered. 8.5 g of this product are introduced into a solution of 12 g of the aniline obtained in step 2, dissolved in 50 ml of dimethylacetamide, at 10° C. The medium is allowed to raise to 20° C. and the solvent is removed by distillation and the residue is washed with diethyl ether. w=16 g.

4. Coupling of the amine prepared in E and hydrazinolysis:

18 g of the amine E, 10 g of the above acid and 3.5 g of HOBT are dissolved in 80 ml of dimethylacetamide at 35° C.; 4.9 g of EDCI.HCl are then introduced into the reaction medium, cooled to 20° C.; after one day, this mixture is poured into 600 ml of dichloromethane and the precipitate formed is washed with 400 ml of ethanol. The precipitate is dissolved in 90 ml of dimethylacetamide and 22 ml of water at 8° C.; 1.85 ml of hydrazine hydrate are then introduced and the medium is stirred for 3 hours, after which the solvents are evaporated off. The residue is dissolved in 800 ml of water and the pH is brought to 1 by addition of aqueous HCl solution (12N). After filtration through Celite® and chromatography on an anionic resin and on a cationic resin, followed by filtration of the eluent through carbon black, 13 g of the desired compound are recovered.

5. Reaction of the products of formulae II and III:

1 g of the chelate A and 8 g of the above amine are dissolved in 40 ml of water. After acidification to pH 6 by addition of dilute aqueous HCl solution, the reaction medium is brought to 40° C. and 0.09 g of sulphonic NHS and 1.2 g of EDCI.HCl are introduced therein. After stirring for 2 hours at this temperature, the medium is poured into 400 ml of ethanol and the precipitate is recovered.

After the usual purification treatments, 6 g of the final product are recovered.

SEC: Above conditions; $t_r$=38 minutes.

EXAMPLE 11

Gadolinium chelate of formula I in which m=2 m=2

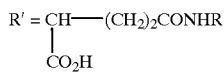
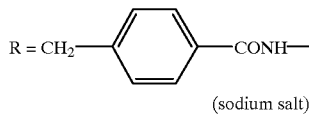
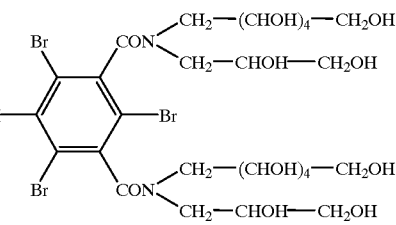

1. 5-(4-Nitrobenzamido)-2,4,6-tribromoisophthalic acid:

50 g of para-nitrobenzoyl chloride and 75 g of 5-amino-2,4,6-tribromoisophthalic acid are refluxed for 18 hours in 400 ml of dioxane. After cooling, the precipitate is filtered off, washed with 50 ml of dioxane and dried. w=115 g.

2. 5-(4-Aminobenzamido)-2,4,6-tribromoisophthalic acid:

A solution of 180 g of the above nitro derivative in 600 ml of water is brought to pH 6 by addition of aqueous 5N NaOH solution and hydrogenated at a pressure of $5 \times 10^5$ Pa in the presence of Pt type 156 (Johnson Matthey) for 7 hours. The catalyst is separated out by filtration and the water is evaporated under reduced pressure. w=80 g.

HPLC: Column No. 1; Eluent No. 6: water/trifluoroacetic acid (pH 2.8) with methanol (99/1-v/v); flow rate 1 ml/min.; $t_r$=3.6 minutes (18.8 minutes for the nitro compound).

3. 5-(4-[4-(Phthalimidomethyl)benzamido]benzamido)-2,4,6-tribromoisophthalic acid:

A mixture of 10 g of 4-aminomethylbenzoic acid, 14.5 g of N-carbethoxyphthalimide and 9.2 ml of triethylamine in 140 ml of tetrahydrofuran is refluxed for 72 hours. The precipitate recovered by filtration at room temperature from the reaction medium is washed with diethyl ether and aqueous 1N hydrochloric acid solution. 14.5 g of solid are obtained, 12.2 g of which are dissolved at 10° C. in 90 ml of N,N-dimethylacetamide and 3.5 ml of thionyl chloride; after stirring for 3 hours, 23.4 g of the aniline obtained in step 2 are introduced into the medium and the mixture is left stirring overnight, after which it is poured into 900 ml of water. The precipitate recovered, washed with water, is recrystallized from 200 ml of dioxane. w=30 g.

HPLC: Column No. 1; Eluent No. 5: water/$CH_3COONH_4$ (0.01 M)/$CH_3CN$;

Flow rate 1 ml/min.; gradient from 85/15 to 50/50 in 20 minutes.

4. Acid dichloride:

30.3 g of the isophthalic derivative obtained in the above step are dissolved in 150 ml of dioxane containing 26 ml of dimethylformamide and, at 5° C., 42 ml of thionyl chloride are introduced dropwise. After 30 minutes at 0° C., the mixture is poured into 550 ml of water and the precipitate formed is filtered off, washed with water and with diisopropyl ether. w=26 g after drying.

5. N,N'-(2,3,4,5,6-Pentahydroxyhexyl)-N,N'-(2,3-dihydroxypropyl)-2,4,6-tribromo-5-[4-(4-aminomethylbenzamido)benzamido]isophthalamide:

(a) 10 g of the acid dichloride are introduced into a solution of 15 g of 1-deoxy-1-(2,3-dihydroxypropylamino)-D-galactitol in 100 ml of N-methylpyrrolidone at 60° C. After stirring for 4 hours at this temperature, the medium, cooled to room temperature, is poured into 1 liter of isopropanol. The precipitate formed is recovered and dried.

HPLC: Column No. 1; Eluent No. 5; $t_r$=16 minutes.

(b) Removal of the phthalimido group:

20.4 g of the above solid are introduced, with stirring, into 80 ml of N,N-dimethylacetamide at 80° C., followed by 1.6 ml of hydrazine hydrate dissolved in 20 ml of water. After 3 hours at this temperature, the reaction medium is poured, at room temperature, into 1 liter of ethanol. The precipitate formed is recovered, dried and then dissolved in 40 ml of water. At 0° C., about 2 ml of aqueous 6N HCl solution are introduced to lower the pH to 2; the medium is filtered through Celite® and then purified by passage through ion-exchange resins (Amberlite® anionic and IMAC® cationic). 6 g of the desired product are thus obtained.

HPLC: Column No. 1; Eluent No. 5; $t_r$=24 to 29 minutes.

6. Reaction with the chelate A:

5.8 g of the above amine and 1.1 g of the chelate (sodium salt) are dissolved in 12.5 ml of water and the pH is lowered to 6 by addition of aqueous 1N HCl solution. 12.5 ml of dioxane, 0.06 g of HOBT and then 1.8 g of EDCI are introduced and the medium is maintained at pH 6 for 4 hours, after which it is poured into 150 ml of ethanol. The precipitate formed is recovered and then purified by tangential ultrafiltration on a 50 cm² regenerated cellulose membrane with a cutoff threshold of 30 KD (Labscale® module from Millipore®). 5.6 g of the expected product are thus recovered.

HPLC: Column No. 1; Eluent No. 3; $t_r$=16 minutes.

EXAMPLE 12

Gadolinium chelate of formula I in which

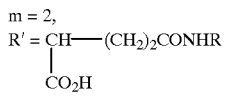
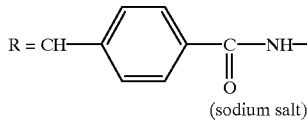
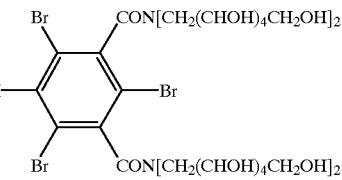

1. N,N'-bis(2,3,4,5,6-Pentahydroxyhexyl)-2,4,6-tribromo-5-[4-(4-aminomethylbenzamido)benzamido]isophthalamide:

(a) A solution of 10 g of the acid dichloride prepared as in step 4 of Example 11 and 20.6 g of disorbitylamine in 200 ml of N-methylpyrrolidone is stirred for 4 hours at 60° C. The reaction medium is then introduced into 1.5 liters of isopropanol, from which 17.5 g of precipitate are recovered.

HPLC: Column No. 1; Eluent No. 5; $t_r$=15 minutes.

(b) Removal of the phthalimido group:

The process is performed as in the above example, starting with 16 g of the product from step (a), to give 6.2 g of the expected amine.

HPLC: Column No. 1; Eluent No. 2; $t_r$=15 to 20 minutes.

2. The process is performed as in Example 11 above, starting with 0.78 g of chelate A and 4.8 g of amine, to give 2.5 g of the expected product.

HPLC: Column No. 1; Eluent No. 3; $t_r$=13 minutes.

EXAMPLE 13

Gadolinium chelate of formula I in which

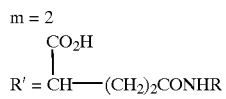
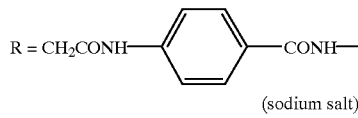
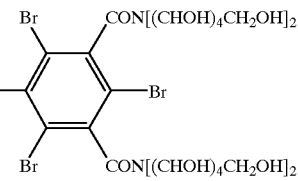

1. 4-(Phthalimidomethylcarbonylamino)benzoic acid:

3.9 ml of thionyl chloride are introduced, at 10° C., into a solution of 10 g of phthaloylglycine in 30 ml of N,N-dimethylacetamide, followed, after stirring for 3 hours at this temperature, by 4 g of 4-aminobenzoic acid. After leaving overnight at room temperature, the medium is poured into 500 ml of water at 80° C. The precipitate formed is recovered.

2. 5-(4-[4-(Phthalimidomethylcarbonylamino) benzamido]benzamido)-2,4,6-tribromoisophthalic acid:

4.8 ml of thionyl chloride are introduced, at 10° C., into a solution of 19.5 g of the above acid in 120 ml of N,N-dimethylacetamide, followed, after 2 hours 30 min, by 38 g of 5-(4-amino)benzamido-2,4,6-tribromoisophthalic acid. After leaving overnight at room temperature, the medium is poured into 1 liter of water and the precipitate formed is recovered and washed with 400 ml of hot dioxane. w=7.4 g.

3. N,N'-bis(2,3,4,5,6-Pentahydroxyhexyl)-2,4,6-tribromo-5-(4-(4-[phthalimidomethylcarbonylamino] benzamido)benzamido)isophthalamide:

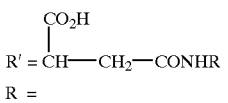
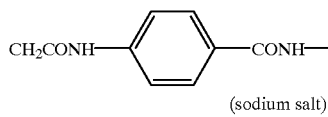
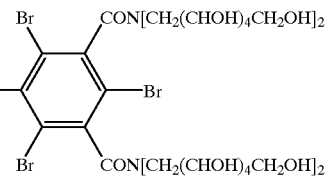

(sodium salt)

21 ml of thionyl chloride are introduced, at 5° C., into a solution of 16.5 g of the above diacid in 90 ml of dioxane and 13.6 ml of dimethylformamide. After stirring for 2 hours 30 min, the medium is poured into 400 ml of water and the precipitate formed is dried and then introduced into a solution, at 70° C., of 29.3 g of disorbitylamine in 150 ml of N-methylpyrrolidone. After stirring for 4 hours at this temperature, the medium is cooled to room temperature, the salts are recovered and the filtrate is poured into 1 liter of isopropanol. The precipitate formed is washed with 1.2 liters of ethanol. w=23 g.

HPLC: Column No. 1; Eluent No. 2; $t_r$=28 to 33 minutes.

4. Removal of the phthalimido group:

22 g of the above phthalimide and 1.4 ml of hydrazine hydrate are introduced into a mixture of 80 ml of N,N-dimethylacetamide and 20 ml of water at 80° C. After 3 hours at this temperature, the medium is cooled to about 20° C. and is then poured into 300 ml of ethanol. The precipitate formed is dried and dissolved in 40 ml of water, the solution is cooled to 0° C. and 3 ml of 6N hydrochloric acid are added to pH 1.5. After filtration through Celite®, the filtrate is eluted through 45 ml of Amberlite® IRA67 anionic resin (Rohm & Haas), 50 ml of IMAC® HPIIIE cationic resin and then 16 ml of Amberlite® IRA458 anionic resin. After neutralization and filtration through a 0.22 μm membrane, the solution is brought to dryness. w=11.7 g.

HPLC: Column No. 1; Eluent No. 2; $t_r$=16 to 20 minutes.

5. Coupling with the chelate A:

11.2 g of the above amine and 1.9 g of the chelate A (sodium salt) are dissolved in 24 ml of water. The pH of the solution is brought to 6.1 by addition of aqueous 2N HCl solution. 24 ml of dioxane are then added, followed by 2.7 g of 1-(3-dimethylaminopropyl)-3-ethylcarbodiimide hydrochloride and 0.094 g of hydroxybenzotriazole. After stirring for 3 hours at room temperature, the mixture is poured into 300 ml of ethanol and the precipitate formed is recovered. After ultrafiltration with a Labscale® module, whose membrane has a cutoff threshold of 10 KD, the solution is freeze-dried. w=10.2 g.

HPLC; Column No. 1; Eluent No. 7: $CH_3CN$/P.I.C. A* (Waters®) gradient for 25 minutes from 25/75 to 30/70;

P.I.C. A=$H_2O/H_3PO_4/(C_4H_9)_4N^+HSO_4^-$;

$t_r$=14 minutes.

EXAMPLE 14

Gadolinium chelate of formula I in which m=1

1.8 g of the gadolinium chelate of (1,4,7,10-tetraazacyclododecane)-1,4,7,10-tetra(2-succinic) acid and 13.5 g of N,N'-bis(2,3,4,5,6-pentahydroxyhexyl)-2,4,6-tribromo-5-(4-[4-aminoacetamidobenzamido] benzoylglycylamino)isophthalamide prepared as in step f of Example 3 are dissolved in 70 ml of water and aqueous 1N HCl solution is introduced to pH 6. After addition of 2 g of EDCI, the mixture is maintained at 40° C. for 2 hours. Tangential ultrafiltration is then carried out on a Minisette® Filtron® module containing a polyether sulphone membrane with a cutoff threshold of 5 KD, up to 2 liters of filtrate; the retentate is then placed in contact for 2 hours with 15 g of Darco® G60 black sold by Aldrich®. After separation of the carbon black by filtration and concentration to dryness, 5 g of white solid are recovered.

SEC: Conditions No. 1; $t_r$=35 minutes.

What is claimed is:

1. Chelate of a cation of a paramagnetic metal with a compound of formula

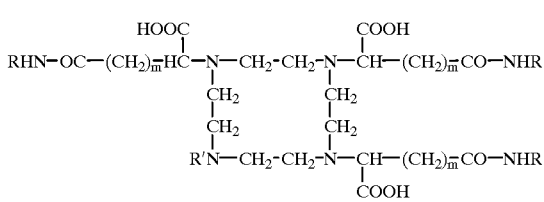

I in which m is 1 or 2,

R' is selected from the group consisting of H, a $C_1$–$C_4$ alkyl or hydroxyalkyl group, a group $CH_2$—COOH and a group $CH_2$—$CONZ_1Z_2$, $Z_1$ and $Z_2$ being, independently of each other, H or an optionally hydroxylated $C_1$–$C_4$ alkyl group, or R' is a group

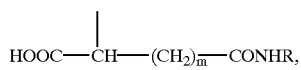

R is a group

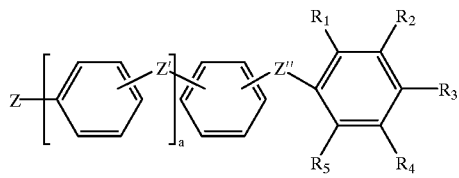

in which a is 1 or 2

Z is selected from the group consisting of a bond, $CH_2$, $CH_2CONH$ and $(CH_2)_2NHCO$ Z' is selected from the group consisting of a bond, O, S, NQ, $CH_2$, CO, CO—NQ, NQ—CO, NQ—CO—NQ and CO—NQ—$CH_2$—CONQ Z" is selected from the group consisting of CO—NQ, NQ—CO, CO—NQ—$CH_2$—CO—NQ and NQ—CO—$CH_2$—NQ—CO where Q is H or an optionally hydroxylated $C_1$–$C_4$ alkyl group $R_1$, $R_2$, $R_3$, $R_4$ and $R_5$, independently of each other, are selected from the group consisting of H, Br, Cl, I, CO—$NQ_1Q_2$ and $N(Q_1)$—CO—$Q_2$ and $Q_1$ and $Q_2$ are independently selected from $C_2$–$C_6$ alkyl groups which are optionally interrupted by an oxygen atom, wherein at least one of $Q_1$, $Q_2$ is hydroxylated such that $Q_1$ and $Q_2$ together contain from 4 to 10 OH groups, with the proviso that at least 1, and not more than 2, groups $R_1$, $R_2$, $R_3$, $R_4$ and $R_5$ are amido groups, and the salts thereof with a pharmacologically acceptable organic base or inorganic base.

2. Chelate of a cation of a paramagnetic metal with a compound of formula I, and the salts thereof, according to claim 1, in which m is 2
R' is

a is 1,

Z is selected from the group consisting of a bond, $CH_2$ and $CH_2CONH$,

Z' is selected from the group consisting of CONH, NHCO, CONH—$CH_2$—CONH and NHCONH, Z" is selected from the group consisting of CONH and CONH—$CH_2$—CONH, and then $R_2$=$R_4$=$CONQ_1Q_2$ or $R_3$=$CONQ_1Q_2$ and $R_1$, $R_2$, $R_4$ and $R_5$ are H, Br, Cl or I, or Z" is NHCO, and then $R_2$=$R_4$=$N(Q_1)COQ_2$ or $R_3$=N$(Q_1)$—$COQ_2$ and $R_1$, $R_2$, $R_4$ and $R_5$ are H, Br, Cl or I.

3. Chelate of a paramagnetic metal cation of a compound of formula I, and the salts thereof, according to claim 1, in which m is 2,
R' is

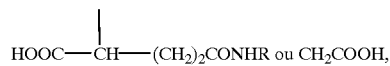

a is 1,

Z is selected from the group consisting of a bond, $CH_2$ and $CH_2CONH$,

Z' is selected from the group consisting of CONH, NHCONH and CONH—$CH_2$—CONH,

Z" is selected from the group consisting of CONH and CONH—$CH_2$—CONH, $R_1$, $R_3$ and $R_5$ are all Br or I, $R_2$ and $R_4$ are $CONQ_1Q_2$ where $Q_1$ and $Q_2$ are selected from $C_2$–$C_6$ hydroxyalkyl groups together containing 6 to 10 OH groups or containing 4 to 8 OH groups if $Q_1$ and/or $Q_2$ is interrupted by an oxygen atom.

4. Chelate of a paramagnetic metal cation of a compound of formula I, and the salts thereof, according to claim 1, in which m is 2,
R' is

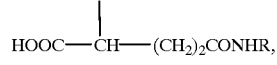

a is 1,

Z is selected from the group consisting of $CH_2$ and $CH_2CONH$,

Z' is selected from the group consisting of CONH and NHCONH,

Z" is selected from the group consisting of CONH and CONH—$CH_2$—CONH, $R_1$, $R_3$ and $R_5$ are all Br or I, $R_2$ and $R_4$ are $CONQ_1Q_2$ where $Q_1$ and $Q_2$ are selected from $C_2$–$C_6$ hydroxyalkyl groups together containing 6 to 10 OH groups or containing 4 to 8 OH groups if $Q_1$ and/or $Q_2$ is interrupted by an oxygen atom.

5. Chelate of a paramagnetic metal cation of a compound of formula I, and the salts thereof, according to claim 1, in which m is 2,
R' is

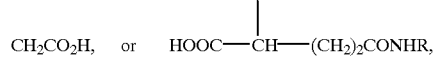

a is 1,

Z is selected from the group consisting of $CH_2$ and $CH_2CONH$,

Z' and Z" are CONH, $R_1$, $R_3$ and $R_5$ are all Br or I, $R_2$ and $R_4$ are $CONQ_1Q_2$ where $Q_1$ and $Q_2$ are selected from $C_2$–$C_6$ hydroxyalkyl groups together containing 6 to 10 OH groups or containing 4 to 8 OH groups if $Q_1$ and/or $Q_2$ is interrupted by an oxygen atom.

6. Chelate of a paramagnetic metal cation of a compound of formula I, and the salts thereof, according to claim 1, in which m is 2,
R' is $$CH_2CO_2H, \quad \text{or} \quad HOOC-\overset{|}{CH}-(CH_2)_2CONHR,$$

a is 2,
Z is selected from the group consisting of $CH_2$ and $CH_2CONH$,
Z' is selected from the group consisting of CONH and NHCO,
Z" is selected from the group consisting of CONH and CONH—$CH_2$—CONH,

[structure: $CH_2CONH$—C$_6$H$_4$—CONH—C$_6$H$_4$—CONH—C$_6$H$_4$—CONH]

and $R_1$, $R_3$ and $R_5$ are all Br or I,
and then $R_2$ and $R_4$ are both $CONQ_1Q_2$,
or $R_3$ is $CONQ_1Q_2$, and then $R_1$, $R_2$, $R_4$ and $R_5$ are H, Br or I.

7. Chelate of a paramagnetic metal cation of a compound of formula I, and the salts thereof, according to claim 1, in which m is 1,
R' is $$HOOC-\overset{|}{CH}-CH_2-CONHR,$$

a is 1,
Z is selected from the group consisting of $CH_2$ and $CH_2CONH$,
Z' is CONH,
Z" is selected from the group consisting of CONH and CONH—$CH_2$—CONH,
$R_1$, $R_3$ and $R_5$ are Br,
$R_2$ and $R_4$ are $CONQ_1Q_2$, where $Q_1$ and $Q_2$ are $C_2$–$C_6$ hydroxyalkyl groups together containing from 6 to 10 OH groups.

8. Chelate according to claim 1, in which the metal cation is $Gd^{3+}$.

9. Gadolinium chelate, and the salts thereof, of the compound of formula I according to claim 1, in which m is 2, $$R' = HOOC-\overset{|}{CH}-(CH_2)_2CONHR$$

and R is

[structure with Br, $CON[CH_2(CHOH)_4CH_2OH]_2$ groups]

10. Gadolinium chelate, and the salts thereof, of the compound of formula I according to claim 1, in which m is 2
R' is $$HOOC-\overset{|}{CH}-(CH_2)_2CONHR$$

[structure: R = Z—C$_6$H$_4$—CONH—C$_6$H$_4$—Z"—ring with $R_1$, $R_3$, $R_5$, $CONQ_1Q_2$, $CONQ_1Q_2$]

where Z" is CONH—$CH_2CONH$ and $Q_1$ and $Q_2$ are $CH_2(CHOH)_4CH_2OH$, in which case either Z is $CH_2$ and $R_1$, $R_3$ and $R_5$ are I, or Z is $CH_2CONH$ and $R_1$, $R_3$ and $R_5$ are Br, or where Z" is CONH, Z is selected from the group consisting of $CH_2$ and $CH_2CONH$ and $R_1$, $R_3$ and $R_5$ are Br and $Q_1$ is $CH_2(CHOH)_4CH_2OH$, and $Q_2$ is $CH_2CHOH$—$CH_2OH$ or $CH_2(CHOH)_4CH_2OH$.

11. Contrast agent for diagnostic magnetic resonance imaging, comprising an effective amount of a chelate according to claim 1 in a pharmaceutically acceptable vehicle.

12. Scintigraphy agent containing a radio-labelled chelate of a metal cation with a compound of formula

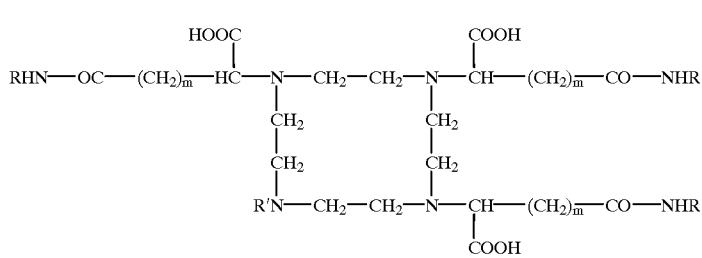

in which
- m is selected from the group consisting of 1 and 2,
- R' is selected from the group consisting of H, a $C_1$–$C_4$ alkyl or hydroxyalkyl group, and a group $CH_2$—COOH or $CH_2$—$CONZ_1Z_2$, $Z_1$ and $Z_2$ being, independently of each other, H or an optionally hydroxylated $C_1$–$C_4$ alkyl group, or R' is a group

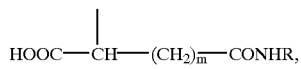

R is a group

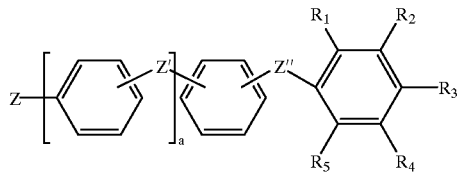

in which a is 1 or 2
- Z is selected from the group consisting of a bond, $CH_2$, $CH_2CONH$ and $(CH_2)_2NHCO$
- Z' is selected from the group consisting of a bond, O, S, NQ, $CH_2$, CO, CO—NQ, NQ—CO, NQ—CO—NQ and CO—NQ—$CH_2$—CONQ
- Z" is selected from the group consisting of CO—NQ, NQ—CO, CO—NQ—$CH_2$—CO—NQ and NQ—CO—$CH_2$—NQ—CO
- where Q is H or an optionally hydroxylated $C_1$–$C_4$ alkyl group
- $R_1$, $R_2$, $R_3$, $R_4$ and $R_5$, independently of each other, are selected from the group consisting of H, Br, Cl, I, CO—$NQ_1Q_2$ or $N(Q_1)$—CO—$Q_2$ and $Q_1$ and $Q_2$ are independently selected from $C_2$–$C_6$ alkyl groups which are optionally interrupted by an oxygen atom, wherein at least one of $Q_1$, $Q_2$ is hydroxylated such that $Q_1$ and $Q_2$ together contain from 4 to 10 OH groups, with the proviso that at least 1, and not more than 2, groups $R_1$, $R_2$, $R_3$, $R_4$ and $R_5$ are amido groups, and the salts thereof with a pharmacologically acceptable organic base or inorganic base.

* * * * *